(12) United States Patent
Levine et al.

(10) Patent No.: US 7,776,593 B2
(45) Date of Patent: Aug. 17, 2010

(54) HES6 AS A MARKER OF PANCREATIC ENDOCRINE CELLS

(75) Inventors: Fred Levine, Del Mar, CA (US); Bjoern Tyrberg, San Diego, CA (US)

(73) Assignee: The Regents of the University of California, Oakland, CA (US)

(*) Notice: Subject to any disclaimer, the term of this patent is extended or adjusted under 35 U.S.C. 154(b) by 39 days.

(21) Appl. No.: 11/835,391

(22) Filed: Aug. 7, 2007

(65) Prior Publication Data

US 2008/0119435 A1    May 22, 2008

Related U.S. Application Data

(60) Provisional application No. 60/821,698, filed on Aug. 7, 2006.

(51) Int. Cl.
  *C12N 5/08* (2006.01)
  *C12N 5/06* (2006.01)
  *C12Q 1/68* (2006.01)
  *C07K 16/00* (2006.01)
  *C07H 21/04* (2006.01)

(52) U.S. Cl. .................. 435/370; 435/6; 435/325; 435/363; 435/366; 530/387.9; 536/23.5

(58) Field of Classification Search ............ 435/6, 435/325, 363, 366, 370; 436/501; 530/388.24, 530/387.9; 536/23.5
See application file for complete search history.

(56) References Cited

U.S. PATENT DOCUMENTS

2005/0053588 A1*  3/2005  Yin .................... 424/93.21
2006/0040389 A1*  2/2006  Murry et al. ............. 435/377

OTHER PUBLICATIONS

Baum, "Solid Phase Synthesis of Benzodiazepines," C&EN, p. 33-34, 18 Jan. 1993.
Beattie et al., "Sustained Proliferation of PDX-1+ Cells Derived from Human Islets." *Diabetes*, 48:1013-19, 1999.
Beatus et al., "The Notch 3 Intracellular Domain Represses Notch 1-Mediated Activation through *Hairy/Enhancer of split* (*HES*) Promoters." *Development*, 126:3925-35, 1999.
Berdnik et al., "The Endocytic Protein alpha-Adaptin is Required for Numb-Mediated Asymmetric Cell Division in Drosophila." *Dev Cell.*, vol. 3, pp. 221-231, 2002.
Chen et al., "*Hop* Is an Unusual Homeobox Gene that Modulates Cardiac Development." *Cell*, 110: 713-23, 2002.
D.R.W. Group, "Conquering Diabetes: A Strategic Plan for the 21st Century." *NIH Publication No. 99-4398*, National Institutes of Health, 1999.
Fior et al., "A Novel hes5/hes6 Circuitry of Negative Regulation Controls Notch Activity During Neurogenesis." *Dev Biol.*, 281: 318-33, 2005.
Fujikura et al., "Notch/Rpb-j Signaling Prevents Premature Endocrine and Ductal Cell Differentiation on the Pancreas." *Cell Metab.*, 3: 59-65, 2006.

Gasa et al., "Proendocrine Genes Coordinate the Pancreatic Islet Differentiation Program In Vitro." *Proc Natl Adac Sci USA*, 101: 13245-50, 2004.
Go et al., "Cell Proliferation Control by Notch Signaling in *Drosophila* Development." *Development*, 125: 2031-40, 1998.
Gonos, "Expression of the Growth Arrest Specific Genes in Rat Embryonic Fibroblasts Undergoing Senescence." *Ann N YAcad Sci.*, 851: 466-69, 1998.
Gratton et al., "Hes6 Promotes Cortical Neurogenesis and Inhibits Hes1 Transcription Repression Activity by Multiple Mechanisms." *Mol Cell Biol.*, 23: 6922-35, 2003.
Groth et al., "Xenoislet Transplantation: Experimental and Clinical Aspects." *J. Mol. Med.*, 77:153-4, 1999.
Gu et al., "Direct Evidence for the Pancreatic Lineage: NGN3+ Cells are Islet Progenitors and are Distinct from Duct Progenitors," *Development*, 129: 2447-57, 2002.
Heremans et al., "Recapitulation of Embryonic Neuroendocrine Differentiation in Adult Human Pancreatic Duct Cells Expressing Neurogenin 3." *J Cell Biol.*, 159: 303-12, 2002.
Hua et al., "BMP4 Regulates Pancreatic Progenitor Cell Expansion Through Id2." *J Biol Chem.*, 281: 13574-80, 2006.
Huang et al., "Notch-Induced E2A Degradation Requires CHIP and Hsc70 as Novel Facilitators of Ubiquitination." *Mol Cell Biol.*, 24: 8951-62, 2004.
Itkin-Ansari et al. "Sources of Beta Cells for Human Cell-Based Therapies for Diabetes," *Cell Biochem Biophys.*, 40: 103-112, 2004.
Kenyon et al., "Long-term Survival and Function of Intrahepatic Islet Allografts in Rhesus Monkeys Treated with Humanized anti-CD154." *PNAS USA*, 96:8132-37, 1999.
Ketola et al., "Transcription Factor GATA-6 is Expressed in the Endocrine and GATA-4 in the Exocrine Pancreas." *Mol Cell Endocrinol.*, 226: 51-57, 2004.
Kleeff et al., "Pancreatic Cancer—New Aspects of Molecular Biology Research." *Swiss Surg.*, 6: 231-34, 2000.
Kodama et al., "Enhanced Expression of PDX-1 and Ngn3 by Exendin-4 During Beta Cell Regeneration in STZ-treated Mice." *Biochem Biophys Res Commun.*, 327: 1170-78, 2005.
Koyano-Nakagawa et al., "Hes6 Acts in a Positive Feedback Loop with the Neurogenins to Promote Neuronal Differentiation." *Development*, 127: 4203-16, 2000.
Lee et al., "Regulation of the Pancreatic Pro-Endocrine Gene *Neurogenin3.*" *Diabetes*, 50: 928-36, 2001.
Lee et al., "Regeneration of Pancreatic Islets After Partial Pancreatectomy in Mice Does Not Involve the Reactivation of Neurogenin-3" *Diabetes*, 55: 269-72, 2006.
Levine, "Gene Therapy for Diabetes: Strategies for Beta Cell Modification and Replacement." *Diabetes/Metabolism Reviews* 1: 206-46, 1997.
Liu et al., "Citron Kinase is a Cell Cycle-Dependent, Nuclear Protein Required to G2/M Transition of Hepatocytes." *J Biol Chem.*, 287: 2541-48, 2003.
Norgaard et al., "FGF10 Signaling Maintains the pancreatic progenitor Cell State Revealing a Novel Role of Notch in Organ Development." *Dev. Biol.*, 264: 323-38, 2003.

(Continued)

*Primary Examiner*—Jane Zara
(74) *Attorney, Agent, or Firm*—Townsend and Townsend and Crew LLP.

(57) ABSTRACT

The present invention provides methods of identifying endocrine stem and progenitor cells.

2 Claims, 14 Drawing Sheets

OTHER PUBLICATIONS

Petersen et al., "The Enigma of the Numb-Notch Relationship during Mammalian Embryogenesis." *Dev Neurosci.*, 28: 156-68, 2006.

Pissarra et al., "Expression of *hes6*, a New Member of the Hairy/Enhancer-of-split Family, in Mouse Development." *Mech Dev.*, 95: 275-78, 2000.

Qian et al., "Basic Helix-Loop-Helix Gene Hes6 Delineates the Sensory Hair Cell Lineage in the Inner Ear." *Dev. Dyn.*, 235: 1689-1700, 2006.

Rath et al., "LMCD1/Dyxin Is a Novel Transcriptional Cofactor that Restricts GATA6 Function by Inhibiting DNA Binding." *Mol Cell Biol.*, 25: 8864-73, 2005.

Seta et al., "Notch-Associated Gene Expression in Embryonic and Adult Taste Papillae and Taste Buds Suggests a Role in Taste Cell Lineage Decisions." *J Comp. Neurol.*, 464: 49-61, 2003.

Shin et al., "Modulation of Cardiac Growth and Development by HOP, an Unusual Homeodomain Protein." *Cell*, 110: 725-35, 2002.

Shinozuka et al., "Altered Expression of HES-1, BETA2/NeuroD, and PDX-1 is Involved in Impaired Insulin Synthesis Induced by Glucocorticoids in HIT-T15 Cells." *Biochem Biophys Res Commun.*, 287: 229-35, 2001.

Suzuki et al., "Expression of *Hes6* and *NeuroD* in the Olfactory Epithelium, Vomeronasal Organ and Non-Sensory Patches." *Chem Senses*, 28:197-205, 2003.

Sweeney et al., "Notch 1 and 3 Receptor Signaling Modulates Vascular Smooth Muscle Cell Growth, Apoptosis, and Migration via a CBF-1/RBP-Jk dependent pathway." *FASEB J*, 18: 142103, 2004.

Vasiliauskas et al., "Expression of Mouse *Hes-6*, a New Member of the Hairy/Enhancer of Split Family of bHLH Transcription Factors." *Mech Dev.* 98: 133-37, 2000.

Wang et al., "Analysis of a Human Fetal Pancreatic Islet Cell Line." *Transplant Proc.*, 29: 2219, 1997.

Want et al., "Isolation and Characterization of a Cell Line From the Epithelial Cells of the Human Fetal Pancreas." *Cell Transplant*, vol. 6, No. 1, pp. 59-67, 1997.

Yin et al., "Hop Functions Downstream of Nkx2.1 and GATA6 to Mediate HDAC-Dependent Negative Regulation of Pulmonary Gene Expression." *Am J Physiol Lung Cell Mol Physiol.*, 291: L191-L199, 2006.

Zhang et al., "Inhibition of Activin Signaling Induces Pancreatic Epithelial Cell Expansion and Diminishes Terminal Differentiation of Pancreatic Beta Cells." *Diabetes*, 53: 2024-33, 2004.

* cited by examiner

A.

B.

```
LOCUS       BAA96082      224 aa     linear   PRI 24-FEB-2001
DEFINITION  HES6 [Homo sapiens]
ACCESSION   BAA96082
VERSION     BAA96082.1  GI:8051702
DBSOURCE    accession AB035179.1
KEYWORDS
SOURCE      Homo sapiens (human)
  ORGANISM  Homo sapiens
            Eukaryota; Metazoa; Chordata; Craniata; Vertebrata;
Euteleostomi;
            Mammalia; Eutheria; Euarchontoglires; Primates; Haplorrhini;
            Catarrhini; Hominidae; Homo.
REFERENCE   1
  AUTHORS   Bae,S., Bessho,Y., Hojo,M. and Kageyama,R.
  TITLE     The bHLH gene Hes6, an inhibitor of Hes1, promotes neuronal
            differentiation
  JOURNAL   Development 127 (13), 2933-2943 (2000)
  PUBMED    10851137
REFERENCE   2  (residues 1 to 224)
  AUTHORS   Kageyama,R.
  TITLE     Direct Submission
  JOURNAL   Submitted (20-NOV-1999) Ryoichiro Kageyama, Kyoto University,
            Institute for Virus Research; Shogoin-Kawahara, Sakyo-ku,
Kyoto,
            Kyoto 606-8507, Japan (E-mail:rkageyam@virus.kyoto-u.ac.jp,
            Tel:81-75-751-4011, Fax:81-75-751-4807)
FEATURES             Location/Qualifiers
     source          1..224
                     /organism="Homo sapiens"
                     /db_xref="taxon:9606"
     Protein         1..224
                     /product="HES6"
     CDS             1..224
                     /gene="Hes6"
                     /coded_by="AB035179.1:1..675"
ORIGIN
        1 mappaapgrd rvgrededgw etrgdrkark plvekkrrar ineslqelrl llagaevqak
       61 lenaevlelt vrrvqgvlrg rarereqlqa easerfaagy iqcmhevhtf vstcqaidat
      121 vaaellnhll esmplregss fqdllgdala gpprapgrsg wpaggapgsp ipsppgpgdd
      181 lcsdleeape aelsqapaeg pdlvraalga vttaqiarsv wrpw
```

Figure 14

HES6 AS A MARKER OF PANCREATIC ENDOCRINE CELLS

CROSS-REFERENCES TO RELATED APPLICATIONS

The present application claims priority to U.S. Ser. No. 60/821,698, filed Aug. 7, 2006, herein incorporated by reference in its entirety.

STATEMENT AS TO RIGHTS TO INVENTIONS MADE UNDER FEDERALLY SPONSORED RESEARCH OR DEVELOPMENT

This invention was made with Government support under NIH Grant No. DK068754. The Government has certain rights in this invention.

BACKGROUND OF THE INVENTION

Transplantation of cells exhibiting glucose-responsive insulin secretion has the potential to cure diabetes. However, this approach is limited by an inadequate supply of pancreatic β-cells, the only cells exhibiting the desired property. The development of expanded populations of human β-cells that can be used for cell transplantation is therefore a major goal of diabetes research (D. R. W. Group, "Conquering diabetes: a strategic plan for the 21st century" *NIH Publication No. 99-4398* (National Institutes of Health, 1999)). A number of alternative approaches are being pursued to achieve that goal, including using porcine tissue as a xenograft (Groth et al., *J Mol Med* 77:153-4 (1999)), expansion of primary human β-cells with growth factors and extracellular matrix (Beattie et al., *Diabetes* 48:1013-9 (1999)), and generation of immortalized cell lines that exhibit glucose-responsive insulin secretion (Levine, *Diabetes/Metabolism Reviews* 1: 209-46 (1997)). A need exists, therefore, for methods of identifying and purifying cells that exhibit glucose responsive insulin secretion, and for progenitor and/or stem cells capable of differentiating into glucose-responsive insulin-secreting cells.

SUMMARY OF THE INVENTION

The present invention demonstrates that Hes6, a notch signaling regulatory molecule, is a marker of endocrine stem/progenitor cells. Such cells can differentiate into cells that exhibit glucose responsive insulin secretion. Hes6 can be used in methods for identifying and purifying endocrine stem and progenitor cells. Such cells could then be differentiated, e.g., in culture, into cells that exhibit glucose responsive insulin secretion and used to treat patients with diabetes. Hes6 can also be used as a drug target to identify molecules that stimulate stem and progenitor cells to differentiate or proliferate. Hes6 can also be used to identify cell surface markers on endocrine stem and progenitor cells so that the markers can be used in drug assays and in methods of purifying endocrine stem/progenitor cells, e.g., using FACS. Furthermore, the present invention shows that elimination of Hes6 in the pancreas leads to beta cell regeneration. Inhibition of Hes6, using, e.g., small molecule drugs and siRNA, could be used to promote beta cell regeneration in patients in need of beta cells, e.g., diabetic patients, cancer patients, and transplant candidates.

In one embodiment, the invention provides a method for purifying endocrine stem cells, the method comprising the steps of (a) selecting a starting population of cells to be sorted; (b) detecting the expression of Hes6 in a subset of said starting population of cells; (c) separating cells expressing Hes6 from cells that do not express Hes6, wherein said separated population of cells expressing Hes6 comprises a higher percentage of endocrine stem cells relative to the starting population.

In another embodiment, the invention provides a method for identifying endocrine stem cells, comprising the steps of (a) contacting at least one test cell with a detectable agent specific for Hes6; (b) detecting the presence of Hes6; (c) identifying said test cell as an endocrine stem cell if the presence of Hes6 is detected.

In yet another embodiment, the invention provides a method of identifying a compound that modulates endocrine cell function or promotes endocrine cell proliferation, the method comprising the steps of contacting Hes6 positive cells with the compound and determining the effect of the compound on endocrine cell function.

In another embodiment, a method for regenerating endocrine cells in a subject is provided, wherein the method comprising the step of administering to the subject an effective amount of a compound that inhibits Hes6 expression. In a related embodiment, the inhibitory compound is an siRNA that selectively inhibits Hes6 expression.

BRIEF DESCRIPTION OF THE DRAWINGS

FIG. 14 provides an amino acid sequence of human Hes6 (SEQ ID NO:1).

DETAILED DESCRIPTION OF THE INVENTION

I. Introduction

Figure 1:
FIG. 1. Hes1 and Hes6 expression in MIN6, βlox5, and TRM-6 cells. A. RT-PCR analysis of Hes1 expression in the human pancreatic islet cell lines TRM-6 and βlox5. The data presented are representative of three different assays. Jurkat T cell lymphoma cells did not express Hes1. B. Quantitative RT-PCR analysis of Hes1 and Hes6 levels in TRM6, βlox5, and the mouse insulinoma cell line MIN6. The data presented are representative of multiple independent assays. Normalization to a conserved sequence in GAPDH was used to compare mouse and human mRNA levels.
Figure 1:
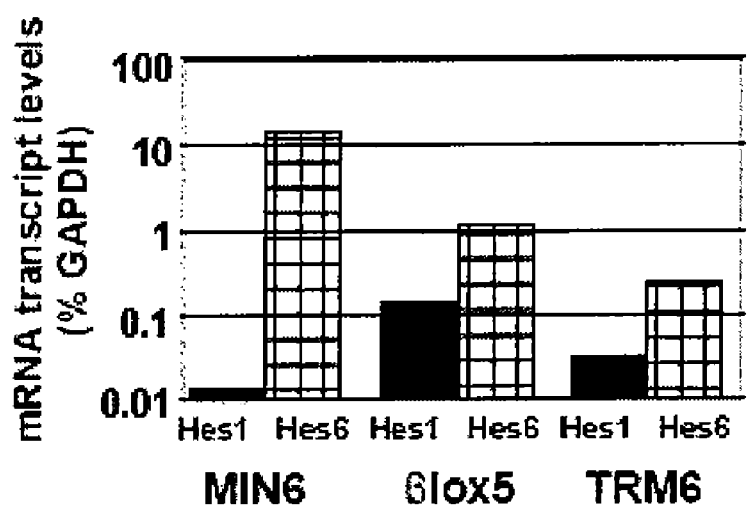

The present invention demonstrates that Hes6 is a marker for endocrine stem and progenitor cells. Thus, Hes6 can be used to purify and identify such cells, which can then be cultured and administered to a patient ex vivo. The cells can be induced to proliferate in vitro or to differentiate into cells that secrete insulin in response to glucose. Hes6 can also be used as a target in a drug assay, wherein the assay is used to identify and select drugs that induce differentiation and/or proliferation of endocrine stem and progenitor cells. Hes6 can also be used to identify cell surface markers on endocrine stem and progenitor cells. Such markers can then be used to purify the cells, e.g., via FACS, and as targets in drug assays. Finally, inhibition of Hes6 can be used to stimulate beta cell regeneration for patients in need thereof, e.g., diabetic patients, trauma patients, transplant candidates, and cancer patients.

The availability of an unlimited source of functional human β-cells has important implications for diabetes. One straightforward application is in exploring aspects of β-cell biology that would benefit from an unlimited, homogeneous source of cells. High-throughput screening for new diabetes drugs is one such application. The cells of the invention can be used, e.g., to screen for small molecules or other compounds that can induce endocrine cell differentiation. In addition, cells such as those described herein can be used in a cell transplantation therapy for diabetes.

II. Definitions

As used herein, the following terms have the meanings ascribed to them unless specified otherwise.

"Stem cells" are undifferentiated cells that have the potential to become a wide variety of specialized cell types including, e.g., endocrine cells and β-cells). Stem cells include, e.g., embryonic stem cells, adult stem cells, progenitor cells, and pancreas-derived multipotent precursor cells as described in, e.g., Seaberg et al., *Nat. Biotechnol.* 22(9):1115-24 (2004).

"Endocrine cell" refers to a cell originally derived from an adult or fetal endocrine gland (e.g., pancreas and islets of langerhans). "Endocrine pancreas cell" refers to a cell originally derived from an adult or fetal pancreas, preferably islet cells. "Cultured" endocrine pancreas cells refers to primary cultures as well as cells that expressed recombinant nucleic acids. Cultured endocrine pancreas cells also refer to cells that have been transformed with oncogenes, e.g., SV40 T antigen, ras, or a telomerase gene (e.g., hTRT).

"Culturing" refers to growing cells ex vivo or in vitro. Cultured cells can be non-naturally occurring cells, e.g., cells that have been transduced with an exogenous gene such as an oncogene or a transcription factor such as NeuroD/BETA2 and/or PDX-1. Cultured cells can also be naturally occurring isolates or primary cultures.

A "stable" cell line or culture is one that can grow in vitro for an extended period of time, such as for at least about 50 cell divisions, or for about 6 months, more preferably for at least about 150 cell divisions, or at least about ten months, and more preferably at least about a year.

"Inducing endocrine cell differentiation" refers to inducing differentiation of an endocrine cell such that the cell expresses genes and cell surface proteins typically expressed by insulin producing β-cells. For example, a "differentiated" endocrine cell typically expresses insulin, glucokinase (GK), granuphilin, chromagranin A, chromogranin C, Synaptotamin-like protein 3, and/or p57/kip2 at a level that is at least about 1 fold higher than an undifferentiated endocrine cell; GK, SUR-1, MafA, insulin, chromogranin C, Synaptotamin-like protein 3, and/or p57/kip2 at a level that is at least about 2 fold higher than an undifferentiated endocrine cell; chromogranin C and/or p57/kip2 at a level that is at least about 10 fold higher than an undifferentiated endocrine cell; p57/kip2 at a level that is at least about 1000 fold higher than an undifferentiated endocrine cell; and/or c-myc at a level that is at least about 1 fold lower than an undifferentiated endocrine cell. Differentiated endocrine cell gene expression can be measured by methods known to those of skill in the art, e.g., by measuring RNA expression, polypeptide production, or cell surface protein expression, e.g., reverse transcription and amplification of mRNA, isolation of total RNA or poly A+ RNA, northern blotting, dot blotting, in situ hybridization, RNase protection, and immunoassays.

Cells committed to a β-cell lineage can often be recognized by testing the cells for expression of β-cell specific gene expression. β-cell specific genes include, e.g., PDX-1. PDX-1 is involved in the regulation of insulin expression. See, e.g., PCT Application No. 01/07628. Therefore, cells expressing PDX-1 are likely committed to β-cell differentiation. Other exemplary β-cell specific genes include, e.g., NKX6.1 (e.g., Sander et al., *Development* 127:5533-5540 (2000)) and PAX4 (e.g., Sosa-Pineda, et al., *Nature* 386:399-402 (1997)). These gene products are typically expressed in β-cells. Other relevant endocrine pancreas gene markers, though not necessarily β-cell specific markers, include, e.g., PAX6 (see, e.g., Larsson, et al., *Mechanisms of Development* 79:153-159 (1998)), NKX2.2 (M. Sander, et al., *Development* 127:5533-5540 (2000)), sulfonylurea receptor (see, e.g., Aguilar-Bryan et al., *Science* 268:423-426 (1995)), the GLP-1 receptor (see, e.g., Salapatek et al., *Mol Endocrinol* 13(8):1305-17 (1999)) and glucokinase (see, e.g., Matschinsky et al., *Diabetes* 47(3):307-15 (1998)).

Cells that "secrete insulin in response to glucose" are cells or a cell culture that, in comparison to a negative control (either non-insulin responsive cells or insulin responsive cells that are not exposed to glucose), have increased insulin secretion in response to glucose of at least about 10%, preferably 25%, 50%, 100%, 500%, 1000%, 5000%, or higher than the control cells (measured as described above).

A "stable" cell line or culture is one that can grow in vitro for an extended period of time, such as for at least about 50 cell divisions, or for about 6 months, more preferably for at least about 150 cell divisions, or at least about ten months, and more preferably at least about a year.

"Modulating β-cell function" refers to a compound that increases (activates) or decreases (inhibits) glucose responsive insulin secretion of an endocrine pancreas cell. Glucose responsive insulin secretion can be measured by a number of methods, including analysis of insulin mRNA expression, preproinsulin production, proinsulin production, insulin production, and c-peptide production, using standard methods known to of skill in the art. To examine the extent of modulation, cells are treated with a potential activator or inhibitor and are compared to control samples without the activator or inhibitor. Control samples (untreated with inhibitors or activators) are assigned a relative insulin value of 100%. Inhibition is achieved when the insulin value relative to the control is about 90%, preferably 75%, 50%, and more preferably 25-0%. Activation is achieved when the insulin value relative to the control is 110%, more preferably 125%, 150%, and most preferably at least 200-500% higher or 1000% or higher.

A diabetic subject is a mammalian subject, often a human subject, that has any type of diabetes, including primary and secondary diabetes, type 1 non-insulin dependent diabetes mellitus (NIDDM)-transient, type 1 insulin-dependent diabetes mellitus (IDDM), type 2 IDDM-transient, type 2 NIDDM, and type 2 maturity onset diabetes of the young (MODY), as described in *Harrison's Internal Medicine,* 14th ed. 1998.

The term "immunoassay" is an assay that uses an antibody to specifically bind an antigen, e.g., ELISA, Western blotting, RIA, immunoprecipitation, fluorescence activated cell sorting, and the like. The immunoassay is characterized by the use of specific binding properties of a particular antibody to isolate, target, and/or quantify the antigen (e.g., insulin). In some embodiments, immunoassays are used to quantify the amount of insulin produced by the differentiated endocrine cells of the invention. In some embodiments, immunoassays are used to assess the markers expressed by the differentiated endocrine cells of the invention.

The terms "overexpress," "overexpression" or "overexpressed" interchangeably refer to a protein or nucleic acid (RNA) that is transcribed or translated at a detectably greater level, in comparison to a control cell. The term includes overexpression due to transcription, post transcriptional processing, translation, post-translational processing, cellular localization (e.g., organelle, cytoplasm, nucleus, cell surface), and RNA and protein stability, as compared to a normal cell. Overexpression can be detected using conventional techniques for detecting mRNA (i.e., RT-PCR, PCR, hybridization) or proteins (i.e., ELISA, immunohistochemical techniques). Overexpression can be 10%, 20%, 30%, 40%, 50%, 60%, 70%, 80%, 90% or more in comparison to a normal cell. In certain instances, overexpression is 1-fold, 2-fold, 3-fold, 4-fold or more higher levels of transcription or translation in comparison to a control cell. Overexpression includes cells that express a nucleic acid or protein as compared to cells that lack expression of the nucleic acid or protein.

The term "Hes6" or "Hes6 polypeptide" refers to polypeptides that have 95% or greater amino acid sequence identity to a polypeptide encoded by a referenced nucleic acid or an amino acid sequence described herein (e.g., the 224 amino acid sequence depicted herein as SEQ ID NO. 1, corresponding to NCBI Database Accession No. BAA96082); (2) specifically bind to antibodies, e.g., polyclonal antibodies, raised against an immunogen comprising a referenced amino acid sequence, immunogenic fragments thereof, and conservatively modified variants thereof. "Hes6 nucleic acids" refers to nucleic acids that have a nucleic acid sequence with greater than about 95%, preferably greater than about 96%, 97%, 98%, 99%, or higher nucleotide sequence identity, preferably over a region of at least about 25, 50, 100, 200, 500, 1000, or more nucleotides, to a reference nucleic acid sequence (e.g., the human gene or human mRNA encoding the polypeptide of SEQ ID NO. 1). A polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention include both naturally occurring or recombinant molecules.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, peptide, circular peptide, lipid, fatty acid, siRNA, polynucleotide, oligonucleotide, etc., to be tested for the capacity to act as a drug. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

"Inhibitors," "activators," and "modulators" of Hes6 polynucleotide and polypeptide sequences are used to refer to activating, inhibitory, or modulating molecules identified using in vitro and in vivo assays. Inhibitors are compounds that, e.g., bind to, partially or totally block activity, decrease, prevent, delay activation, inactivate, desensitize, or down regulate the activity or expression of Hes6 proteins, e.g., antagonists. "Activators" are compounds that increase, open, activate, facilitate, enhance activation, sensitize, agonize, or up regulate Hes6 protein activity, agonists. Inhibitors, activators, or modulators also include genetically modified versions of Hes6 proteins, e.g., versions with altered activity, as well as naturally occurring and synthetic ligands, antagonists, agonists, antibodies, peptides, cyclic peptides, nucleic acids, antisense molecules, ribozymes, RNAi molecules, small organic molecules and the like. Such assays for inhibitors and activators include, e.g., expressing Hes6 protein in vitro, in cells, or cell extracts, applying putative modulator compounds, and then determining the functional effects on activity, as described above.

Samples or assays comprising angiogenesis proteins that are treated with a potential activator, inhibitor, or modulator are compared to control samples without the inhibitor, activator, or modulator to examine the extent of inhibition. Control samples (untreated with inhibitors) are assigned a relative protein activity value of 100%. Inhibition of a protein is achieved when the activity value relative to the control is about 80%, preferably 50%, more preferably 25-0%. Activation of a protein is achieved when the activity value relative to the control (untreated with activators) is 110%, more preferably 150%, more preferably 200-500% (i.e., two to five fold higher relative to the control), more preferably 1000-3000% higher.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

"RNAi molecule" or an "siRNA" refers to a nucleic acid that forms a double stranded RNA, which double stranded RNA has the ability to reduce or inhibit expression of a gene or target gene when the siRNA expressed in the same cell as the gene or target gene. "siRNA" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is 15-50 nucleotides in length, and the double stranded siRNA is about 15-50 base pairs in length, preferable about preferably about 20-30 base nucleotides, preferably about 20-25 nucleotides in length, e.g., 20, 21, 22, 23, 24, 25, 26, 27, 28, 29, or 30 nucleotides in length.

The phrase "functional effects" in the context of assays for testing compounds that modulate activity of a Hes6 protein includes the determination of a parameter that is indirectly or directly under the influence of a Hes6 polypeptide, e.g., a chemical or phenotypic effect; e.g., glucose responsiveness, insulin expression, islet cell marker expression, transcriptional induction of markers or, e.g., a physical effect such as ligand binding or inhibition of ligand binding. Glucose responsive insulin secretion can be measured by a number of methods, including analysis of insulin mRNA expression, preproinsulin production, proinsulin production, insulin production, and c-peptide production, using standard methods known to of skill in the art. "Functional effects" include in vitro, in vivo, and ex vivo activities.

By "determining the functional effect" is meant assaying for a compound that increases or decreases a parameter that is indirectly or directly under the influence of a Hes6 protein, e.g., measuring physical and chemical or phenotypic effects. Such functional effects can be measured by any means known to those skilled in the art, e.g., changes in spectroscopic characteristics (e.g., fluorescence, absorbance, refractive index); hydrodynamic (e.g., shape), chromatographic; or solubility properties for the protein; ligand binding assays, e.g., binding to antibodies; measuring inducible markers or transcriptional activation of the protein; measuring changes in enzymatic activity; measuring changes in cell surface markers; and measuring cellular proliferation, particularly endocrine or islet cell proliferation. The functional effects can be evaluated by many means known to those skilled in the art, e.g., microscopy for quantitative or qualitative measures of alterations in morphological features, e measurement of changes in RNA or protein levels for associated sequences, measurement of RNA stability, identification of downstream or reporter gene expression (CAT, luciferase, β-gal, GFP and the like), e.g., via chemiluminescence, fluorescence, colorimetric reactions, antibody binding, inducible markers, etc.

In one embodiment, cells used in the practice of the invention express one or more oncogenes, such as SV40 T antigen and $Hras^{val12}$, which minimally transform the cells but stimulate growth and bypass cellular senescence. Other suitable oncogenes include, e.g., HPV E7, HPV E6, c-myc, and CDK4 (see also U.S. Pat. No. 5,723,333). In addition, the cells can be transduced with an oncogene encoding mammalian telomerase, such as hTRT, to facilitate immortalization. Suitable oncogenes can be identified by those of skill in the art, and partial lists of oncogenes are provided in Bishop et al., *RNA Tumor Viruses*, vol. 1, pp. 1004-1005 (Weiss et al., eds, 1984), and Watson et al., *Molecular Biology of the Gene* (4$^{th}$ ed. 1987). In some cases the oncogenes provide growth factor-independent and ECM-independent entry into the cell cycle. Often the oncogenes are dominant oncogenes. In some embodiments, the oncogenes are delivered to the cells using a viral vector, preferably a retroviral vector, although any suitable expression vector can be used to transduce the cells (see, e.g., U.S. Pat. No. 5,723,333, which describes construction of vectors encoding one or more oncogenes and transduction of pancreas endocrine cells, see also Halvorsen et al., *Molecular and Cellular Biology* 19:1864-1870 (1999)).

III. Cells of the Invention

The present invention provides methods of inducing differentiation of cells (e.g., embryonic stem cells, adult stem cells, pancreas-derived multipotent cells, and endocrine cells) by purifying the cells using Hes6 as a marker. The cells of the invention may be primary cells or may be cells maintained in culture. Techniques and methods for establishing a primary culture of cells for use in the methods of the invention are known to those of skill in the art. See e.g., Humason, ANIMAL TISSUE TECHNIQUES, 4$^{th}$ ed., W. H. Freeman and Company (1979), and Ricciardelli et al., (1989) *In Vitro Cell Dev. Biol.* 25: 1016. Suitable cells include, for example, endocrine cells and stem cells (e.g., embryonic stem cells, adult stem cells, and pancreas-derived multipotent precursor cells). Suitable endocrine cells include, for example, pancreatic cells, islet cells (e.g., β-cells and δ-cells). Islet cells may be derived from, for example, adult pancreatic tissue, fetal pancreatic tissue and islet-like cell clusters (ICCs) that contain a heterogenous population of cells.

The cells may be derived from any suitable mammal or embryo thereof. For example the cells may be obtained from a rodents such as, for example, mice, rats, guinea pigs, and rabbits; non-rodent mammals such as, for example, dogs, cats, pigs, sheep, horses, cows, and goats; primates such as, for example, chimpanzees and humans.

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

IV. Cell Culture

This invention relies upon routine techniques in the field of cell culture, and suitable methods can be determined by those of skill in the art using known methodology (see, e.g., Freshney et al., *Culture of Animal Cells* (3$^{rd}$ ed. 1994)). In general, the cell culture environment includes consideration of such factors as the substrate for cell growth, cell density and cell contract, the gas phase, the medium, and temperature.

Cells are grown at optimal densities that are determined empirically based on the cell type. Cells are passaged when the cell density is above optimal.

Cultured cells are normally grown in an incubator that provides a suitable temperature, e.g., the body temperature of the animal from which is the cells were obtained, accounting for regional variations in temperature. Generally, 37° C. is the preferred temperature for cell culture. Most incubators are humidified to approximately atmospheric conditions.

Important constituents of the gas phase are oxygen and carbon dioxide. Typically, atmospheric oxygen tensions are used for cell cultures. Culture vessels are usually vented into the incubator atmosphere to allow gas exchange by using gas permeable caps or by preventing sealing of the culture vessels. Carbon dioxide plays a role in pH stabilization, along with buffer in the cell media and is typically present at a concentration of 1-10% in the incubator. The preferred $CO_2$ concentration typically is 5%.

Defined cell media are available as packaged, premixed powders or presterilized solutions. Examples of commonly used media include DME, RPMI 1640, DMEM, Iscove's complete media, or McCoy's Medium (see, e.g., GibcoBRL/Life Tech-nologies Catalogue and Reference Guide; Sigma Catalogue). Typically, low glucose DME or RPMI 1640 are used in the methods of the invention. Defined cell culture media are often supplemented with 5-20% serum, typically heat inactivated, e.g., human horse, calf, and fetal bovine serum. Typically, 10% fetal bovine serum is used in the methods of the invention. The culture medium is usually buffered to maintain the cells at a pH preferably from 7.2-7.4. Other supplements to the media include, e.g., antibiotics, amino acids, sugars, and growth factors such as hepatocyte growth factor/scatter factor.

V. Methods of Treating Diabetic Subjects

The purified cells of the invention can be used to treat diabetic subjects. For example, differentiated endocrine cells produced by the methods described herein are administered to a patient, e.g., a human with type II insulin-dependent diabetes.

In determining the effective amount of the cells to be administered in the treatment or prophylaxis of conditions owing to diminished or aberrant insulin expression, the physician evaluates cell toxicity, transplantation reactions, progression of the disease, and the production of anti-cell antibodies. For administration, cells of the present invention can be administered in an amount effective to provide normalized glucose responsive-insulin production and normalized glucose levels to the subject, taking into account the side-effects of the cell type at various concentrations, as applied to the mass and overall health of the patient. Administration can be accomplished via single or divided doses.

The dose administered to a patient, in the context of the present invention should be sufficient to effect a beneficial therapeutic response in the patient over time. The dose will be determined by the efficacy of the particular cells employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

Immune rejection of grafted cells has previously been a major obstacle to successful islet transplantation. Any universal human donor cell will be recognized by the immune system as an allograft. However, recent advances in therapy for allograft rejection may make this less of a concern (see, e.g., Kenyon et al., *PNAS USA* 96:8132-7 (1999)). An advantage of using a cell line as described herein (immortalized) as a source of transplantable cells is that they can be engineered to exhibit desirable qualities, including avoidance or suppression of host immune responses. Furthermore, autologous cell therapy can be used.

Pharmaceutically acceptable carriers are determined in part by the particular composition being administered (e.g., a cell or small molecule), as well as by the particular method used to administer the composition. Accordingly, there are a wide variety of suitable formulations of pharmaceutical compositions of the present invention (see, e.g., *Remington's Pharmaceutical Sciences*, 17$^{th}$ ed., 1989).

Formulations suitable for parenteral administration, such as, for example, by intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by direct surgical transplantation under the kidney, intraportal administration, intravenous infusion, or intraperitoneal infusion. Injection solutions and suspensions can be prepared from sterile powders, granules, and tablets.

VI. Assays for Modulators of Endocrine Cell Function

In some embodiments, Hes6-expressing cells as described herein are used to identify additional modulators of endocrine cell function.

A. Assays

Assays using the cells of the invention can be used to test for modulators (e.g., inhibitors and activators) of endocrine cell function (e.g., β-cell function or δ-cell function), e.g., by expression of GK, SUR-1, MafA, insulin, granuphilin, chromagranin A, chromogranin C, Synaptotamin like protein 3; (including, e.g., glucose responsive insulin production), granuphilin, chromagranin A, chromogranin C, Synaptotamin like protein 3 production. Such modulators are useful for treating various disorders involving glucose metabolism, such as diabetes and hypoglycemia. Treatment of dysfunctions include, e.g., diabetes mellitus (all types); hyperinsulinism caused by insulinoma, drug-related, e.g., sulfonylureas or excessive insulin, immune disease with insulin or insulin receptor antibodies, etc. (see, e.g., *Harrison's Internal Medicine* (14$^{th}$ ed. 1998)).

Modulation is tested using the cultures of the invention by measuring changes in marker expression (RNA or protein) nor insulin production. Physical or chemical changes can be measured to determine the functional effect of the compound on endocrine cell function. Samples or assays that are treated with a potential inhibitor or activator are compared to control samples without the test compound, to examine the extent of modulation.

In some embodiments, the cells are transfected with a reporter gene operably linked to an appropriate promoter prior to contacting the cells with a potential modulator. Expression of the reporter gene indicates that the test compound is a modulator of β-cell function. Suitable reporter genes include, e.g., green fluorescent protein (GFP), chloramphenicol acetyltransferase gene, a firefly luciferase gene, a bacterial luciferase gene, a β-galactosidase gene, or an alkaline phosphatase gene. Suitable promoters include, e.g., the insulin promoter (see, e.g., Pino et al., *Mol. Endocrinol.* 19(5):1343-60 (2005) and Odagiri et al., *JBC* 271(4):1909-1915 (1996), the PDX-1 promoter (see, e.g., Sander et al., *J. Mol. Med.* 71:327-340 (1997) and Wu et al., *Molecular and Cellular Biology* 17:6002-6013 (1997)), and the Neuro D/Beta-2 promoter (see, e.g., U.S. Pat. No. 5,795,723; Miyachi et al., *Mol. Brain Res.* 69, 223-231 (1999); Lee et al., *Science* 268:836-844 (1995); Wilson et al., *Nature* 368, 32-38 (1994); Naya et al., *Genes Dev.* 9:1009-1019 (1995)).

B. Modulators

The compounds tested as modulators of endocrine cell function (e.g., β-cell function or δ-cell function) can be any small chemical compound, or a macromolecule, such as a protein, sugar, nucleic acid or lipid. SiRNA molecules can also be used to inhibit Hes6 and thereby promote regeneration of endocrine cells. Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *PNAS USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science*, 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

The assays can be solid phase or solution phase assays. In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 96 modulators. If 1536 well plates are used, then a single plate can easily assay from about 100-about 1500 different compounds. It is possible to assay many plates per day; assay screens for up to about 6,000, 20,000, 50,000, or 100,000 or more different compounds are possible using the integrated systems of the invention.

VIII. Detection of Hes6 Positive Cells

Hes6 positive cells can be detected by any means known in the art. RNA and protein can be detected and visualized using antibodies or antisense nucleic acids that specifically recognize Hes6 and which are conjugated to detectable chemical labels, e.g., fluorescent labels, radioactive labels, etc.

IX. Detailed Description of System for Evaluating Hes6

Ngn3 is an important transcription factor expressed in endocrine progenitor cells. Using cell lines derived from the human endocrine pancreas (P Itkin-Ansari and F Levine, *Cell Biochem Biophys*, 40:103-12 (2004); P Itkin-Ansari et al., *Dev Dyn*, 233:946-953 (2005); D Dufayet de la Tour et al., *Mol Endocrinol*, 15:476-483 (2001); P Itkin-Ansari et al., *Mol Endocrinol*, 14:814-22 (2000)), a number of downstream targets of the important transcription factor have been identified. One of those, Hes6, appears to play a central role in regeneration in the adult pancreas as evidenced by mice with homozygous Hes6 mutations.

Theoretically, β-cell regeneration can occur either by neogenesis, i.e., β-cell differentiation from a stem cell, or by replication of preexisting β-cells. It is also known that non-endocrine epithelial cells from the human pancreas have the ability to undergo endocrine differentiation.

Notch signaling plays a critical role at a number of different levels of cell fate determination. It is important in controlling the maintenance of progenitor pools and in controlling alternative cell fates of otherwise apparently identical starting populations of progenitor cells. It is most studied in the nervous system where the decision to commit to a neural versus glial fate is controlled by Notch signaling through lateral inhibition (N Gaiano and G Fishell, *Annu Rev Neurosci*, 25:471-90 (2002)). Commitment to neural cell subtypes is also controlled by the Notch pathway. In the pancreas, ablation of Notch signaling leads to pancreatic hypoplasia, loss of exocrine pancreatic tissue, and premature endocrine differentiation (A Apelqvist et al., *Nature*, 400:877-81 (1999); J Jensen et al., *Nat Genet*, 24:36-44 (2000); E Lammert et al., *Mech Dev*, 94:199-203 (2000); J Fujikura et al., *Cell Metab*, 3:59-65 (2006)).

The general model for Notch signaling is that ligand activation of the transmembrane Notch receptor suppresses the expression of pro-differentiation bHLH proteins such as Ngn3. Transmembrane proteins at the cell surface initiate Notch signaling by binding of a ligand of the Delta and Jagged/Serrate families to a Notch receptor (4 Notch family members in humans and rodents). Ligand binding is modulated by glycosyltransferases of the Fringe family. Engagement of Notch by a ligand triggers a complex series of cleavage steps of Notch near or within the transmembrane domain. The protease that mediates the final cleavage of Notch is thought to be γ-secretase, the same enzyme that cleaves the amyloid precursor protein that plays a key role in the pathogenesis of Alzheimer disease (O Berezovska et al., *Ann N Y Acad Sci*, 920:223-6 (2000)). Presenilin, which is mutated in some cases of familial Alzheimer disease, possesses γ-secretase activity (M S Wolfe, *J Neurochem*, 76:1615-20 (2001)) and is present in the pancreas (D J Figueroa et al., *J Alzheimers Dis*, 3:393-396 (2001)). Once Notch has been cleaved, the intracellular domain translocates to the nucleus, where it binds to the transcription factor RBP-Jκ (also known as CBF1 and suppressor of Hairless or Su(H)). This association converts the transcription factor RBP-Jκ from a repressor to an activator and downstream target genes are then expressed. Predominant among those downstream targets of RBP-Jκ are members of the Hes family of basic helix-loop-helix (bHLH) transcriptional repressors.

Hes family members act by multiple mechanisms. They can form homo- and heterodimers with each other and bind directly to promoters to repress transcription. They can also form heterodimers with other bHLH factors such as the insulin transactivator E47, resulting in potent functional repression. In the pancreas, Hes-1 is a major downstream Notch effector with important targets that include tissue-specific bHLH transcription factors, including Ngn3. Ngn3 is induced in endocrine progenitors when Notch signaling is downregulated and plays an essential role in pancreatic endocrine cell differentiation during fetal development (4), at least in part by inducing the expression of other positively acting bHLH factors, including NeuroD1.

The Notch pathway is subject to complex patterns of activation and feedback regulation. For example, Hes-1 feeds back upon itself to repress its own transcription (K Takebayashi et al., *J Biol Chem*, 269:5150-6 (1994)) and also represses Ngn3 (J C Lee et al., Diabetes, 50:928-36 (2001)). Notch activation inhibits the expression of Notch ligands, separating cells in which Notch is active from cells expressing Notch ligands. It is the existence of multiple auto-regulatory loops that allow the Notch pathway to behave as a switch that can dictate alternative cell fates from closely apposed cells, i.e., lateral inhibition. Brief activation of Notch signaling can be sufficient to produce a commitment to a particular lineage.

A number of repressors have been described that regulate Notch signaling. In some but not all systems Notch3 represses Hes transcription by out-competing Notch1 intracellular domain (Notch1ICD) for binding to RBPJκ (P Beatus et al., *Development*, 126:3925-35 (1999); C Sweeney et al., *FASEB J*, 18:1421-3 (2004)). There is, however, contradictory data indicating that Notch3 acts as an activator rather than an inhibitor of Notch-signaling. Numb is another factor that may inhibit Notch signaling via binding to NotchICD, targeting it for degradation (D Berdnik et al., *Dev Cell*, 3:221-31 (2002)). Numb is critical for cell fate determination in drosophila, but the mechanism by which it antagonizes Notch-signaling is likely to be much more complex than as a direct inhibitor (P H Petersen et al., *Dev Neurosci*, 28:156-68 (2006)). Numb is expressed in mouse pancreatic epithelium from e10.5 and forward (T Yoshida et al., *Differentiation*, 71:486-95 (2003)), but homozygous deletion does not have a major effect on pancreatic development. The fringe glycosyltransferases regulates Notch signaling by modifying Notch proteins but can act both to promote or repress signaling, depending on the ligand (R S Haltiwanger and P Stanley, *Biochim Biophys Acta*, 1573:328-35 (2002)).

Of particular importance for this invention is Hes6, which is a bHLH transcription factor like Hes1. Hes6 has been identified as one of the genes most highly upregulated by Ngn3 over-expression (R Gasa et al., *Proc Natl Acad Sci USA*, 101: 13245-50 (2004)). Hes6 expression has been studied most extensively in the nervous system where it is expressed in neural precursors and is downstream of proneural genes (L Pissarra et al., *Mech Dev*, 95:275-8 (2000); D Vasiliauskas and C D Stern, *Mech Dev*, 98:133-7 (2000); Y Seta et al., *J Comp Neurol*, 464:49-61 (2003); N Koyano-Nakagawa et al., *Development*, 127:4203-16 (2000)). In the vomeronasal organ, it is co-expressed with NeuroD (Y Suzuki et al., *Chem Senses*, 28:197-205 (2003)).

Functionally, Hes6 inhibits the interaction of Hes1 with TLE1, leading to inhibition of Hes1 DNA binding and its repression of pro-neural/endocrine genes. Hes6 also promotes proteolytic degradation of Hes1 (M O Gratton et al., *Mol Cell Biol*, 23:6922-35 (2003)). The chick Hes6 homologue has been shown to inhibit transcription of Hes5, which is a Notch effector similar to Hes1 (R Fior and D Henrique, *Dev Biol*, 281:318-33 (2005)). In contrast to Notch3, Numb and the Fringe proteins, Hes6 appears to be a pure and direct inhibitor in the Notch signaling cascade.

Analysis of the role of the Notch pathway in forming the endocrine pancreas has come primarily through analysis of knockout and transgenic mice with mutations in members of the Notch signaling pathway. A striking finding of those studies has been that all of the mice that have been generated with mutations in the Notch pathway have virtually identical pancreatic phenotypes, i.e., pancreatic hypoplasia with premature endocrine development (A Apelqvist et al., *Nature*, 400: 877-81 (1999); J Jensen et al., *Nat Genet*, 24:36-44 (2000); J Fujikura et al., *Cell Metab*, 3:59-65 (2006)). Thus, Notch signaling within the endocrine pancreas has generally been depicted as a simple linear pathway. However, the complete story is likely to be more complex, particularly in the adult pancreas. Because of the importance of Notch signaling in endocrine cell formation during fetal development, it was reasonable to hypothesize that it would similarly be important in β-cell differentiation in the adult. However, a recent study found very limited endocrine differentiation when neurogenin-3, a downstream effector in the Notch pathway, was expressed in adult duct cells (Y Heremans et al., *J Cell Biol*, 159:303-12 (2002)). In fact, there is controversy about the role of Ngn3 in the adult, with some studies indicating that Ngn3 is induced during β-cell regeneration (G Gu et al., *Development*, 129:2447-57 (2002); S Kodama et al., *Biochem Biophys Res Commun*, 327:1170-8 (2005)) while other studies find no evidence for Ngn3 expression in β-cell regeneration (C S Lee et al., *Diabetes*, 55:269-72 (2006)).

Using a different approach to studying the role of Notch signaling in the adult pancreas, Notch activation by targeted expression of the Notch1 intracellular domain (Notch1ICD) did not affect β-cell differentiation or function. Similarly, β-cell specific ablation of Notch signaling by targeted deletion of CSL also had little effect (J Fujikura et al., *Cell Metab*, 3:59-65 (2006)). These studies have been interpreted as indicating that Notch signaling does not play an important role in β-cell homeostasis under normal circumstances in the adult. However, complete ablation of the pathway or the use of Notch1ICD which, as pointed out by the previous reviewer of this grant, has pleiotropic effects, are blunt instruments that may not reveal the true situation. The pattern of Hes6 expression in the adult pancreas and the effect of Hes6 homozygous mutation on β-cell replication and pancreas regeneration indicate that Notch signaling is playing an important role in regeneration in the adult pancreas. The model system described herein, in which regeneration is upregulated and hence easy to detect, provides the opportunity to gain important insights into that process.

EXAMPLES

The following examples show that Hes6 plays an important role in pancreatic and endocrine cell regeneration and may mark cells that give rise to new pancreatic and endocrine tissue. The following examples are provided by way of illustration only and not by way of limitation. Those of skill in the art will readily recognize a variety of noncritical parameters that could be changed or modified to yield essentially similar results.

Example 1

Identification of Novel Down-stream Targets of Ngn3

Two cell lines have been developed from the human endocrine pancreas, TRM-6 and βlox5, and characterized in detail. TRM-6 was derived from human fetal islets (P Itkin-Ansari et al., *Mol Endocrinol*, 14:814-22 (2000); S Wang et al., *Transplant Proc*, 29:2219 (1997)), while βlox5 was derived from FACS-purified human β-cells (D Dufayet de la Tour et al., *Mol Endocrinol*, 15:476-483 (2001)). These cell lines were developed using the growth stimulatory genes SV40 T antigen, H-ras$^{val12}$, and hTERT (D Dufayet de la Tour et al., *Mol Endocrinol*, 15:476-483 (2001); P Itkin-Ansari et al., *Mol Endocrinol*, 14:814-22 (2000); S Wang et al. *Cell Transplant*, 6:59-67 (1997); T L Halvorsen et al., *Mol Cell Biol*, 19:1864-70 (1999)). Retroviral vector mediated expression of PDX-1 and aggregation of TRM-6 into cell clusters to promote cell-cell contact induced substantial levels of somatostatin expression and at the same time caused partial cell cycle exit (P Itkin-Ansari et al., *Mol Endocrinol*, 14:814-22 (2000)). NeuroD1 potently inhibited somatostatin expression in TRM-6 cells expressing PDX-1. NeuroD1 is not expressed in 8-cells, and in fact is β-cell restricted in the islet (P Itkin-Ansari et al., *Dev Dyn*, 233:946-953 (2005)).

TRM-6 exhibited high levels of Notch pathway activation, as manifested by expression of the bHLH transcriptional repressor Hes1 (FIG. 1). βlox5, which in early passages had exhibited β-cell differentiation in response to PDX-1, cell-cell contact, and activation of the GLP-1 receptor (D Dufayet de la Tour et al., *Mol Endocrinol*, 15:476-483 (2001)), but which in later passages became refractory (P Itkin-Ansari and F Levine, *Cell Biochem Biophys*, 40:103-12 (2004); P Itkin-Ansari et al., *Ann N Y Acad Sci*, 1005:138-47 (2003)), expressed even higher levels of Hes1 (FIG. 1). Hes1 expression in the mouse insulinoma cell line MIN6, which retains a high degree of differentiated function, was low compared with that in βlox5 and TRM-6 (FIG. 1B). Hes1 inhibits cellular differentiation at least in part through potent repression of E-box activation (K Fujimori et al., *J Biol Chem* (2002)). Independently, Notch activation causes degradation of the class I bHLH factor E47, which activates transcription through E-boxes, by a ubiquitination-dependent mechanism (Z Huang et al., *Mol Cell Biol*, 24:8951-62 (2004)).

Induction of Ngn3 as a consequence of Notch inactivation is a crucial step in development of the endocrine pancreas. To identify transcriptional targets of Ngn3 and be able to judge which genes are direct targets of Ngn3 and which might be regulated through NeuroD, βlox5 (D Dufayet de la Tour et al., *Mol Endocrinol*, 15:476-483 (2001)) was infected with adenoviral vectors expressing Ngn3 or NeuroD. Uninfected βlox5 cells as well as cells infected with Ad-GFP were used as controls. Gene expression profiles of these samples, as well as human islets and the non-endocrine fraction of human pancreas (NEPCs), were determined with Illumina Bead microarrays. All samples were analyzed at least in duplicate, most of them in triplicate or more. Gene expression profiles were further analyzed with GeneSpring software.

Data were first analyzed with ANOVA and about 800 genes were determined to be differentially expressed by Ngn3 compared to control (a pool of non-infected and GFP infected cells as these samples were very similar in expression (not shown)). Of those genes, about 200 were up-regulated. Pathway analyses were performed so that pathways with a statistically significant over-representation of genes changes by Ngn3 were identified (FIG. 2A). Several pathways such as TGF-signaling and cell-cycle related genes were identified in this analysis. Genes determined to be of particular interest from the Pathway analyses included BMP-4, SMAD6, cornichon homologue (CNIH3) and Inhibin beta E (INHBE, Activin βE), all members of the TGF-signaling pathway. BMP4 was recently shown to promote Id2 binding to NeuroD (H Hua et al., *J Biol Chem*, 281:13574-80 (2006)); Smad6 is often over-expressed in pancreatic ductal carcinoma (J Kleeff et al., *Swiss Surg*, 6:231-4 (2000)) and inhibition of activin signaling leads to decreased endocrine differentiation (Y Q Zhang et al., *Diabetes*, 53:2024-33 (2004)). Several cell cycle related genes such as GAS-1/3 (E S Gonos, *Ann N Y Acad Sci*, 851:466-9 (1998)) and citron (H Liu et al., *J Biol Chem*, 278:2541-8 (2003)) were also induced by Ngn3. Ngn3+ cells rapidly cease proliferating.

Figure 2:
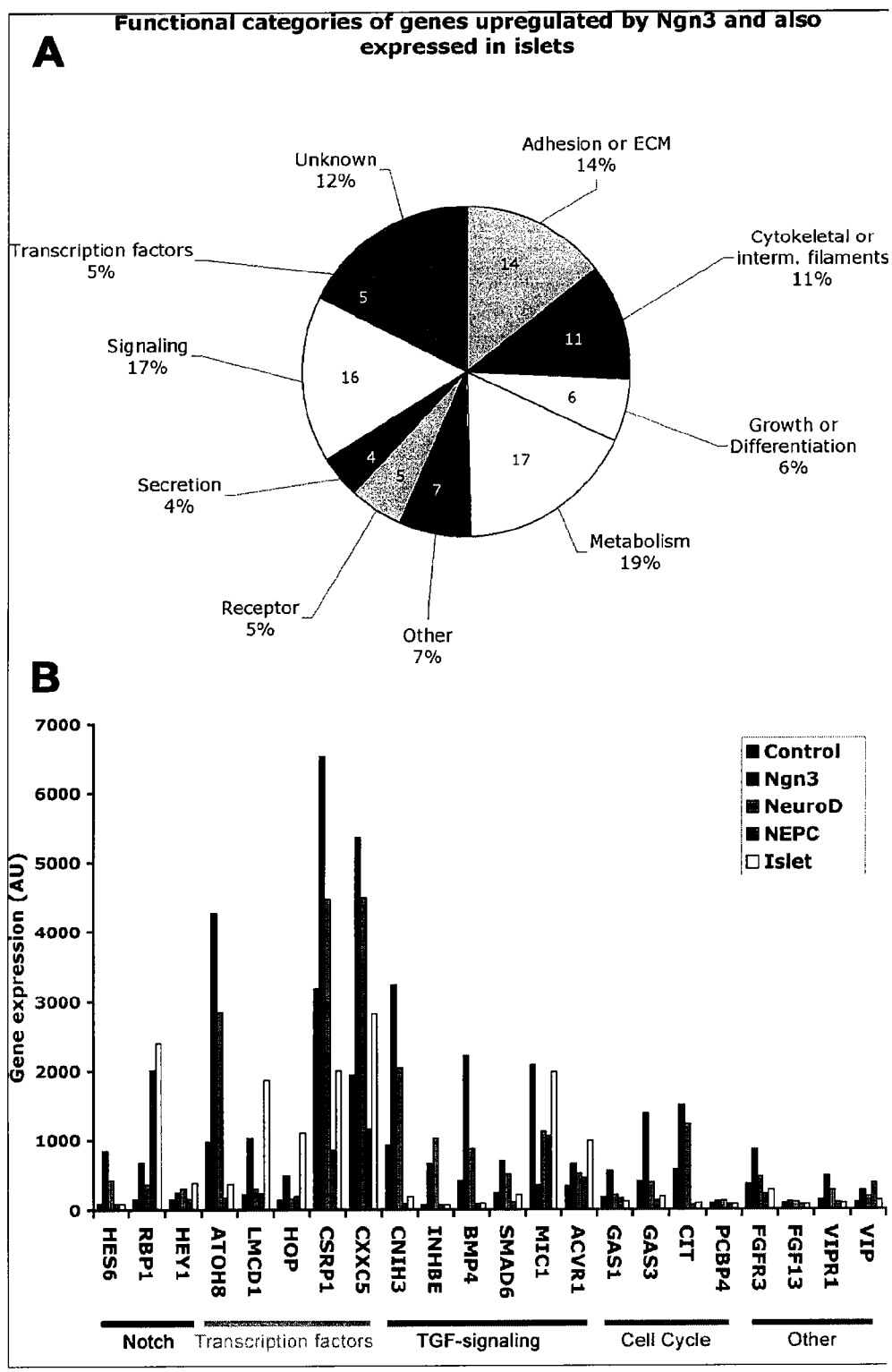
FIG. 2. Gene expression changes in response to Ngn3. Panel A shows how genes upregulated by Ngn3 and also expressed in islets are distributed among functional categories. Panel B shows some of the genes significantly changed by Ngn3 and how they relate in expression to cells over-expressing NeuroD as well as primary pancreatic islets and non-endocrine pancreatic cells (NEPCs).
Figure 3:
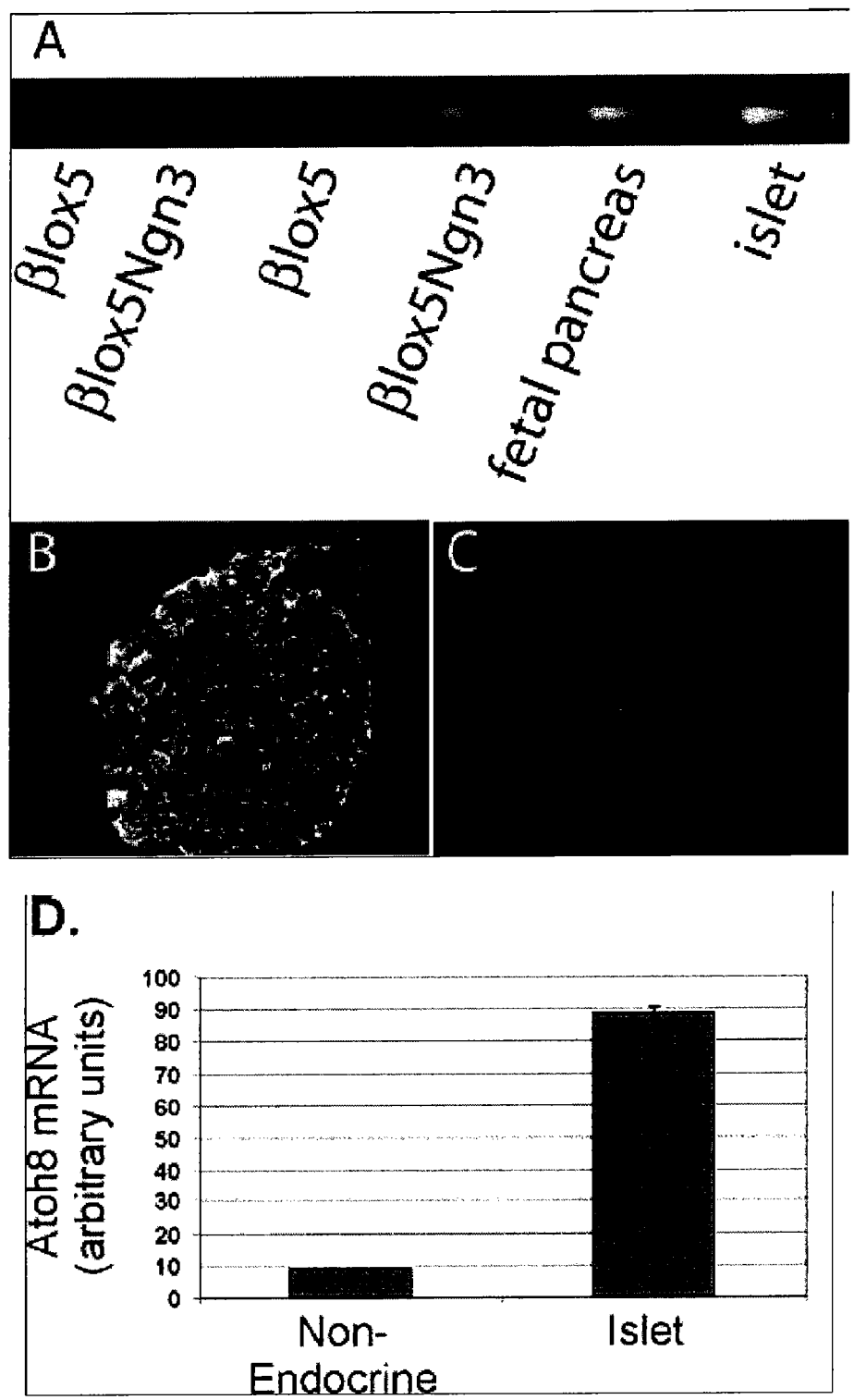
FIG. 3. Expression of selected Ngn3 downstream targets. A. Ngn3 induces HOP in βlox5 cells. HOP is also expressed in fetal pancreas and isolated islets. RT-PCR, 30 cycles. B. LMCD1/dyxin is highly expressed in adult islets (Green-dyxin, Red-insulin, Blue-Glucagon; Dyxin antibody was a kind gift from Dr. E. Morrisey). C. Negative control. (Blue-DAPI; Green, Red and FarRed secondary antibodies). D. Atoh8 is preferentially expressed in islets. RNA from highly purified islet and nonislet cells (1) was used to measure Atoh mRNA levels by real time RT-PCR.
Figure 4:
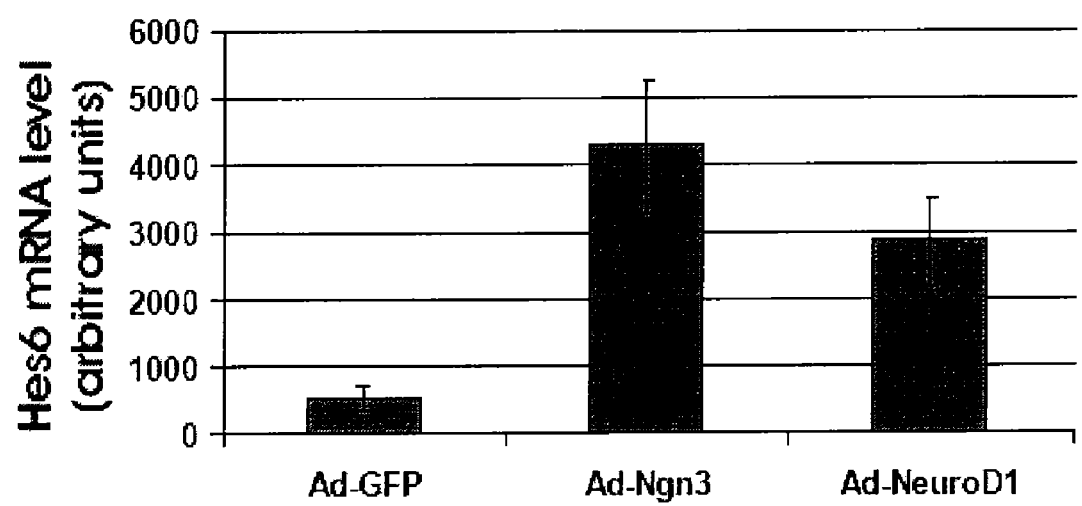
FIG. 4. Hes6 is induced by Ngn3 and NeuroD1. Illumina BeadArray microarray analysis of Hes6 expression in βlox5 cells infected with adenoviral vectors expressing GFP, Ngn3, or NeuroD1. These data were confirmed in multiple assays by RT-PCR (not shown).

A subset of the genes ascertained by the Pathway and Ontology analyses are depicted in FIG. 2B. Analyses based on ontological classification revealed a number of novel transcription factors. HOP is a homeodomain protein involved in transcriptional modulation in heart development. HOP acts down-stream of Nkx2.5 in the heart and Nkx2.1 in airway epithelium (F Chen et al., *Cell*, 110:713-23 (2002); C H Shin et al., *Cell*, 110:725-35 (2002); Z Yin et al., *Am J Physiol Lung Cell Mol Physiol* (2006)), suggesting that it may be dependent on other Nkx proteins in the pancreas, such as Nkx2.2 or 6.1. Both these transcription factors are crucial for endocrine pancreas development (M Sander et al., *Development*, 127:5533-40 (2000)), suggesting that HOP might play a central role as well. HOP expression was confirmed by PCR (FIG. 3A). ATOH8 is a bHLH transcription factor in the same family as Ngn3 (also known as Atoh5) that has not previously been identified in the pancreas. As predicted by the array data from the cell lines, it is selectively expressed in islets (FIG. 3D). LMCD1/dyxin and CSRP1, LIM-domain proteins related to Isl-1; and CXXC5, a zinc-finger transcription factor were also identified. Neither HOP nor LMCD1 were upregulated by NeuroD as determined by parallel studies with an adenoviral vector expressing NeuroD1, suggesting that these genes are specific downstream targets of Ngn3. Both HOP and LMCD1 were highly enriched in islets compared to NEPCs. LMCD1/dyxin restricts GATA6 DNA-binding, providing a potential connection to HOP, which may be dependent on GATA6 in some tissues (Z Yin et al., *Am J Physiol Lung Cell Mol Physiol* (2006); N Rath et al., *Mol Cell Biol*, 25:8864-73 (2005)). GATA6 is restricted to the endocrine compartment in pancreas, whereas GATA4 is exocrine specific (I Ketola, *Mol Cell Endocrinol*, 226:51-7 (2004)). LMCD1/dyxin expression in islets has been confirmed by immunostaining (FIG. 3B-C).

A relatively large number of genes with unknown function were also found (not shown). All genes that were identified as changes by Ngn3 were also compared to islets and pancreatic non-endocrine cells (NEPCs), with many but not all demonstrating higher expression in islets (FIG. 2). Genes enriched in the islet fraction compared to the non-endocrine fraction of adult human pancreas are thus more likely to be important in pancreatic endocrine cells than genes not expressed in islets.

Example 2

Notch Pathway Components, Including Hes6, as Downstream Targets of Ngn3

The expression of several genes related to Notch-signaling was affected by Ngn3; including RBP Jκ (RBP1), and HEY1. Of greatest relevance to this invention, Hes6 was one of the most highly upregulated genes in response to both Ngn3 and NeuroD (FIG. 2). Hes6 also acts downstream of another bHLH transcription factor, Math1 (D Qian et al., *Dev Dyn*, 235:1689-700 (2006)), indicating a broader role in regulating Notch-signaling downstream of differentiation-inducing bHLH proteins.

Example 3

Identification of Hes6 in the Fetal and Adult Pancreas

We examined Hes6 expression in e14.5 pancreata from heterozygote Ngn3$^{EGFP}$ mice (a kind gift from Dr. K. Kaestner) to determine that it was present in at least some Ngn3-expressing endocrine precursor cells. To verify antibody specificity, Hes6 expression was investigated in adult mouse *Papillae Circumvallatae* (FIG. 5d), as Hes6 expression previously was demonstrated in this tissue by in situ hybridization (Y Seta et al., *J Comp Neurol*, 464:49-61 (2003)).

Figure 5:
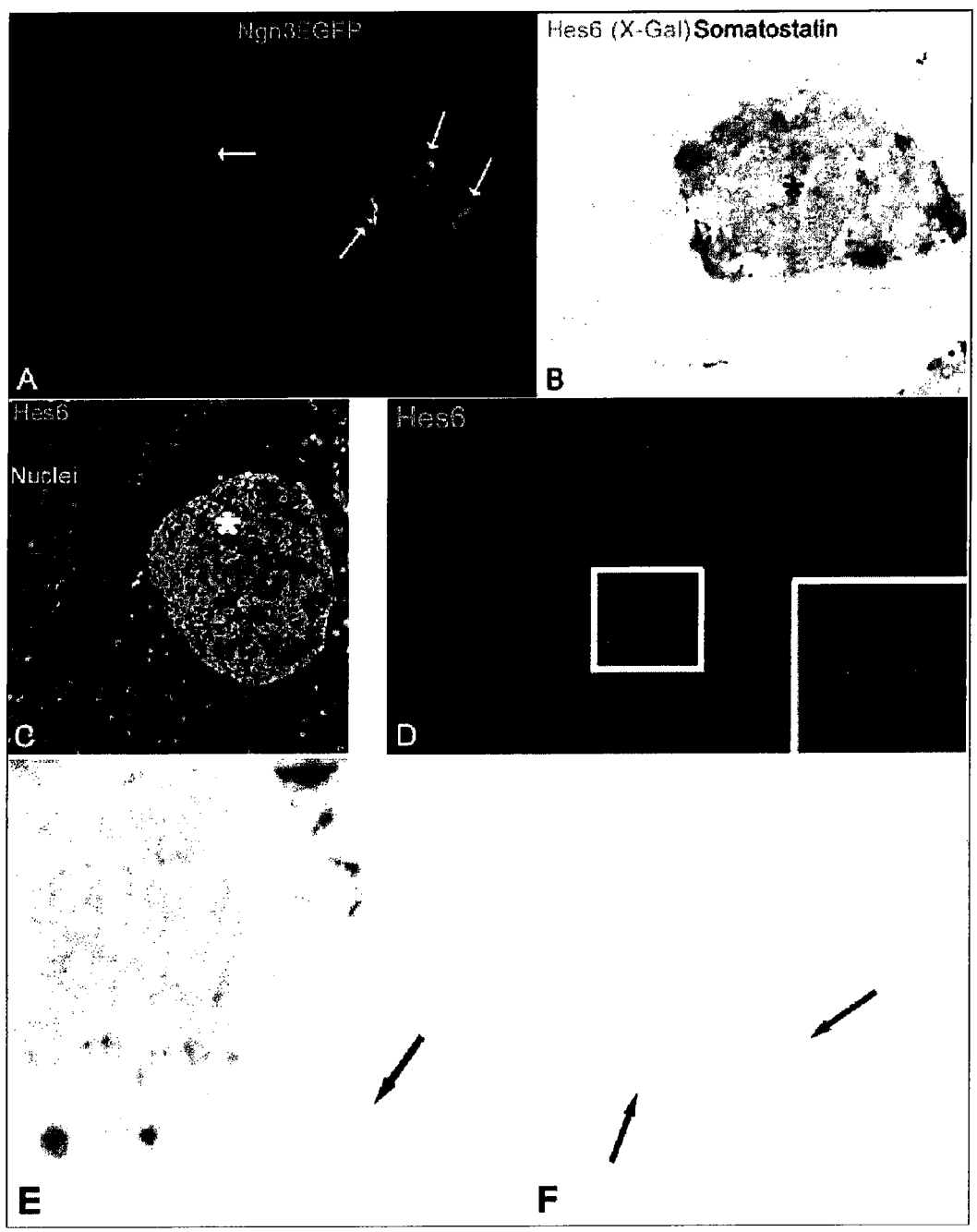
FIG. 5. Hes6 expression in the Pancreas. A. Mouse fetal pancreas (e14.5) expressing EGFP under the control of the Ngn3 promoter, Hes6 (H-180, Santa Cruz, red), Insulin (blue). A subset of Ngn3-EGFP positive cells are also insulin positive and express Hes6 (whitish, arrows). B-C, E-F. Adult mouse pancreas and islets of Langerhans (*). B, E-F. X-Gal histochemical staining (blue) in Hes6$^{tlacZ/+}$ mouse pancreas, demonstrating LacZ (Hes6 promoter activity) in the islets (brown on the edges with somatostatin immuno-labeling), and in some extra-insular cells (E-F, arrows). C. Hes6 (green), Insulin (blue), Amylase (red), nuclei (grey). Green-blue co-localization appears turquoise. D. Verification of Hes6 Ab specificity in mouse taste buds of Papillae Circumvallatae, which has previously been shown to be positive for Hes6 by in situ hybridization.
Figure 6:
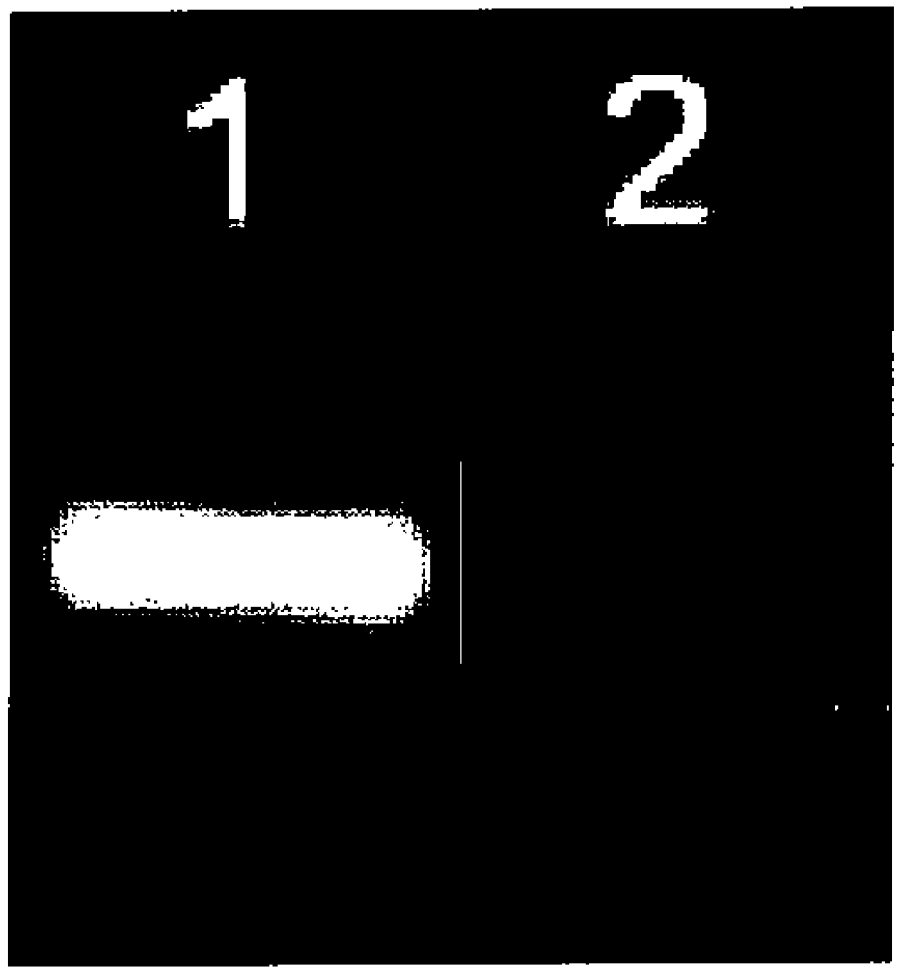
FIG. 6. RT-PCR of isolated mouse islets. 1: Hes6. 2: Minus reverse-transcriptase control for DNA contamination. PCR was conducted for 35 cycles.

Consistent with the data in the cell line model, some Ngn3 (GFP) positive cells expressed Hes6, predominantly in cells also expressing insulin (FIG. 5A). Because Ngn3 is visualized with eGFP under the control of the Ngn3 promoter, this is most consistent with Hes6 being induced by Ngn3, which is then rapidly shut off, while the longer half-life eGFP persists, leading to cells co-expressing insulin, eGFP, and Hes6. Hes6 was also expressed in adult islets demonstrated by lacZ staining in Hes6$^{(tlacZ/+)}$ pancreata and by immunochemistry of wild type pancreata (FIG. 5B-C). Expression of Hes6 was further confirmed by RT-PCR in freshly isolated adult mouse islets of Langerhans (FIG. 6). Together, these data indicate that early endocrine cells turn on Hes6 in response to Ngn3. Hes6 is maintained through development into adulthood. The factors that control continued Hes6 expression are unknown, but may include NeuroD1, which also induces Hes6 expression in our cell line models.

Example 4

Pancreatic Regeneration in Hes6 Homozygous Mutant Mice

Figure 7:
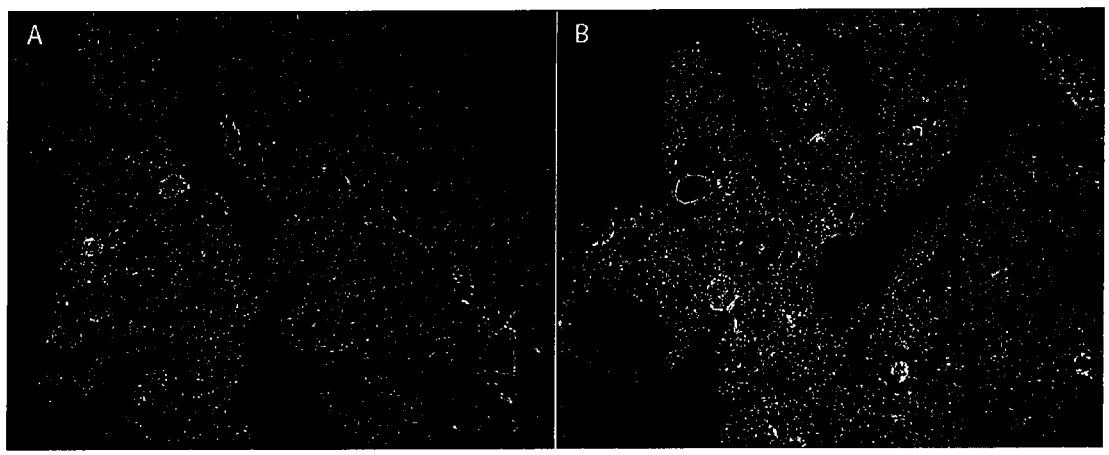
FIG. 7. Islet architecture in Hes6 mutant pancreata. Islet architecture is normal in one month old Hes6 mutant mice (B), compared to wild type (A). Insulin-Blue, Glucagon-Green, Somatostatin-Red, Nuclei-Grey.

The phenotype of the Hes6 homozygous mutant mouse was examined. Those mice, created as a tau-lacZ (tlacZ) knockin in Dr. David Anderson's laboratory, are fertile and grossly normal, although a detailed analysis was not performed (N Koyano-Nakagawa et al., *Development*, 127:4203-16 (2000)). Under unstressed conditions, Hes6 homozygous mutant (Hes6$^{tlacZ/tlacZ}$) mice had a normal pancreatic morphology, including normal appearing islets (FIG. 7). From this, one can conclude either that Hes6 does not play an important role in the adult pancreas, or its role is only revealed under conditions of stress.

To study the role of Hes6 under stressed conditions, mice were placed on a high fat/high calorie diet, more closely resembling a normal human diet. High fat diet in and of itself has been reported to induce islet hyperplasia and regeneration in rodent models (M B Schneider et al., *Gastroenterology*, 120:1263-70 (2001)). In wild-type mice, high fat diet did not have a large effect on β-cell regeneration. However, in the Hes6$^{tlacZ/tlacZ}$ mice, striking abnormalities were observed. Mutant pancreases from mice fed high fat diet exhibited numerous cells co-expressing insulin and amylase (FIGS. 8A-C and 9A-C). Areas with amylase/insulin double-positive cells were common in Hes6 mutants, being found in at least half of the analyzed sections. In mice on a normal diet such cells were not present, irrespective of genotype. Areas with amylase/insulin double-positive cells were morphologically indistinguishable from the normal exocrine pancreas (FIG. 9e-f) and would not have been identified without the insulin/amylase double staining. The amylase-insulin double positive cells resemble mature acinar cells morphologically (FIG. 9H).

Example 5

Hes6 Deficiency and High Fat Diet Act Synergistically to Promote Pancreatic Lobule Neoformation in the Adult In addition to the areas of the pancreas containing amylase/insulin double-positive cells, the high fat fed Hes6$^{tlacZ/tlacZ}$, but not the high fat fed WT animals, had a low frequency of unusual pancreatic lobules (FIG. 8d). Cells within these lobules were highly mitotically active as evidenced by a high rate of Ki67 staining. There were large islets, but minimal staining for exocrine markers. While the etiology of these lobular structures cannot be definitively determined, they appear similar to the new lobules that form following partial pancreatectomy (S Bonner-Weir et al., *Diabetes*, 42:1715-20 (1993)). The fact that they appear only in Hes6$^{tlacZ/tlacZ-}$ homozygous mutant animals suggests that Hes6 plays a role in controlling lobule neoformation.

Figure 13:
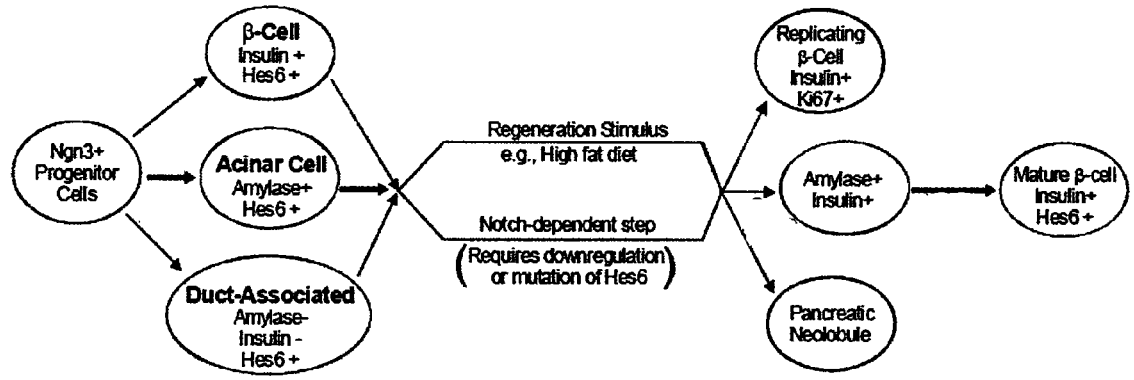
FIG. 13. Role of Hes6 in pancreatic regeneration. Hes6 is induced by Ngn3 and is then expressed in cells of the pancreas that have regeneration potential, including β-cells (by replication), a subset of acinar cells, and a rarer subset of duct-associated cells. In stem/progenitor cells, Hes6 acts as a brake on Notch-signaling, limiting β-cell proliferation, the formation of amylase/insulin double-positive cells and lobule neoformation. Regeneration requires the downregulation of Hes6 and an additional regeneration stimulus.

The finding that the absence of Hes6 leads to increased propensity to form new pancreatic lobules suggests a model in which Hes6 is expressed in a putative stem cell that has the ability to give rise to that lobule (FIG. 13). Such a stem cell could be exceedingly rare, existing in as few as one copy per lobule or perhaps being present only in a subset of lobules. That data here show that Hes6 is a marker of putative cells stem cells that can give rise to new pancreatic lobules. Hes6 functions to repress Notch signaling, maintaining stem cells in a quiescent state. Stimuli for regeneration such as partial pancreatectomy can therefore activate Notch signaling, leading to regeneration on a lobular basis (FIG. 13).

Example 6

Figure 10:
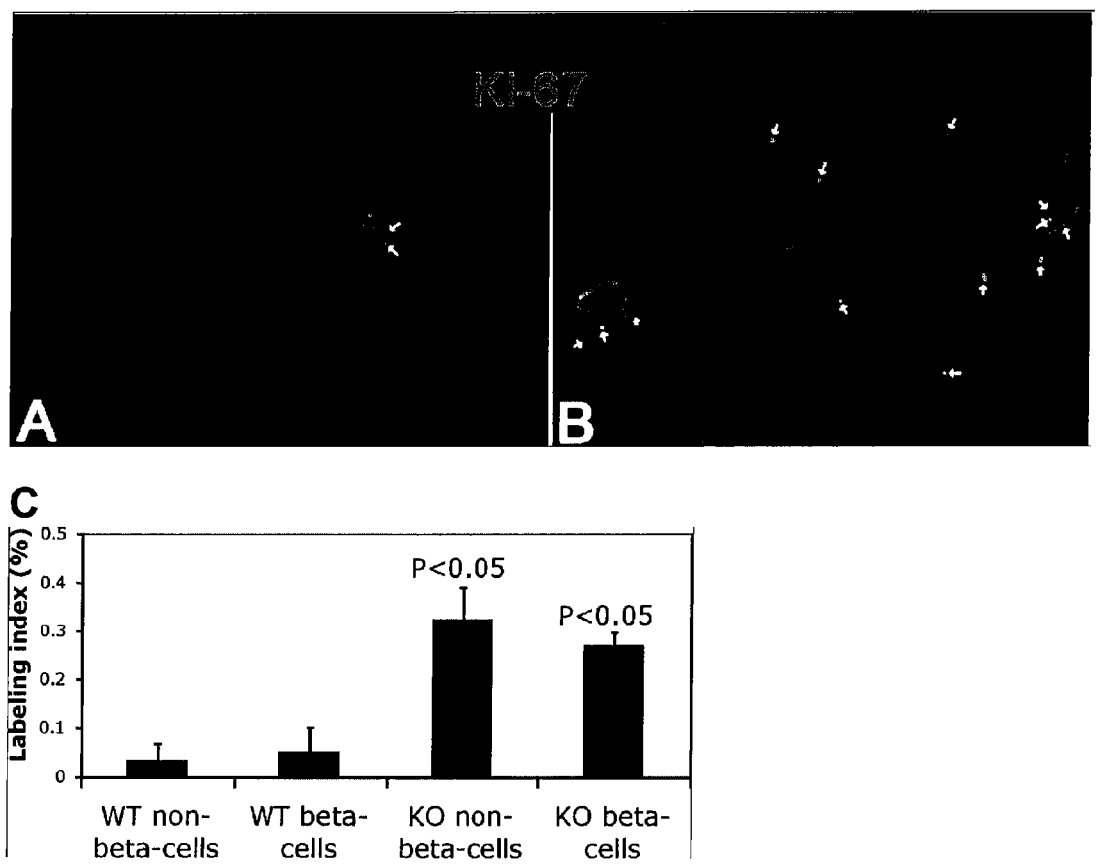
FIG. 10. Hes6 controls endocrine and non-endocrine proliferation in the pancreas. Proliferating cells (Ki-67, white arrows) in pancreata from a Hes6 wild-type (A) and mutant mouse (B) (10×). Adult mice were placed on a high fat diet for 6-8 weeks prior to sacrifice. Pancreas sections were stained for hormones and Ki67. Both non-β-cells and β-cells from mutant mice exhibited a higher proliferation rate than in wild-type (WT) mice. Proliferating cells were very difficult to find in the wild-type pancreas. Quantitation of the extent of proliferation is shown in (D).

Proliferation in Both Endocrine and Non-Endocrine Compartments is Enhanced in Hes6 Mutant Mice Obesity and high fat diet are well known to induce β-cell stress resulting in regeneration and β-cell proliferation in adults (M B Schneider et al., *Gastroenterology*, 120:1263-70 (2001); A Andersson et al., *Metabolism*, 38:974-8 (1989); B Tyrberg et al., *Diabetes*, 50:301-7 (2001)). Because Notch signaling is important in controlling cell cycle entry in many cell types (M J Go et al., *Development*, 125:2031-40 (1998)), the effect of Hes6 deletion on the rate of β-cell replication was examined by staining for the proliferation associated marker Ki67. In Hes6 mutants, β-cell proliferation was increased by 6-7 fold over β-cells in wild-type mice on the same diet (FIG. 10). Increased β-cell proliferation shows that Notch signaling plays an important role in regulating cell cycle entry in β-cells and where Hes6 inhibits β-cell cell cycle entry. Increased cell replication was also observed outside of the islets (FIG. 10). Combined with the previously discussed abnormalities in the exocrine pancreas, Hes6$^+$ cells are fully expected to be present in the extra-islet tissue, as described below.

Example 7

Hes6 is Expressed in Both Endocrine and Non-Endocrine Compartments

Figure 9:
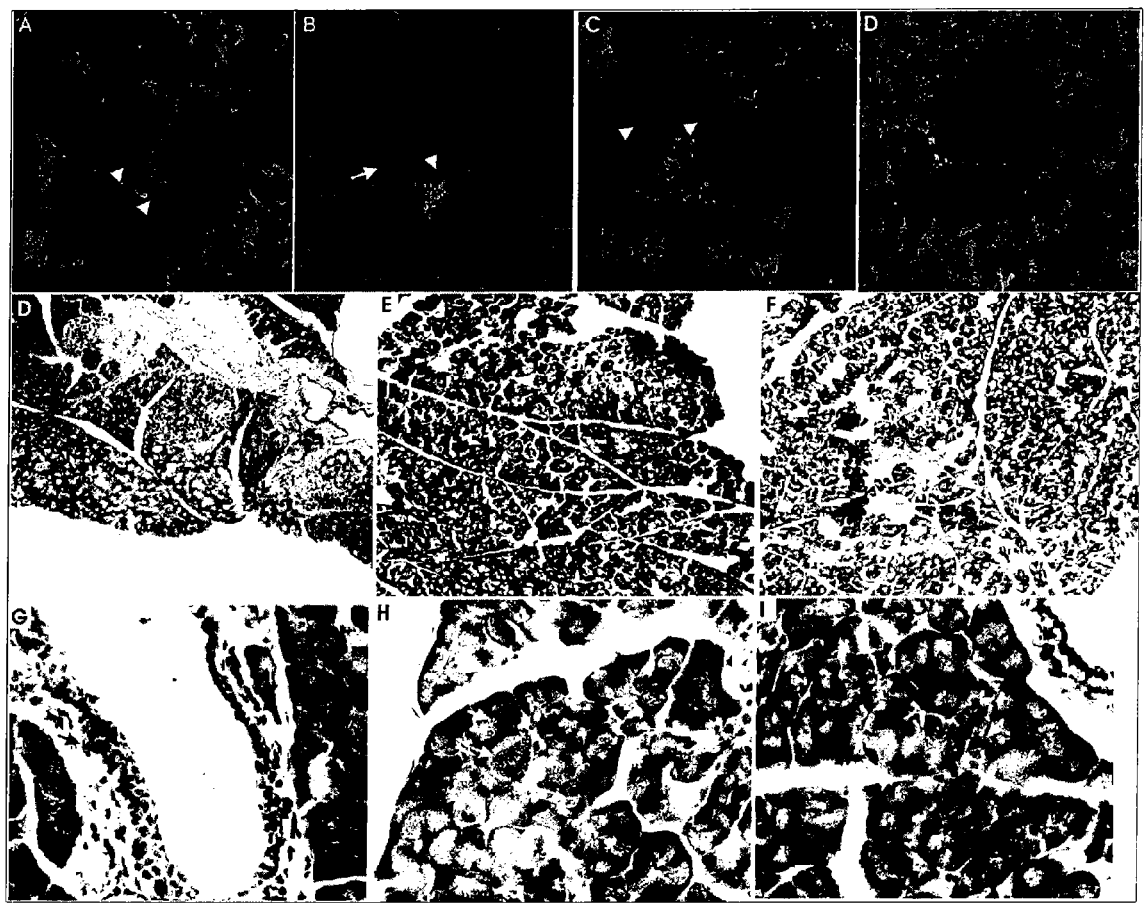
FIG. 9. Further characterization of the adult pancreas in the Hes6 homozygous mutant mouse. Hes6 expression, as assessed by lacZ immunohistochemistry (red) in the Hes6$^{tlacZ/tlacZ}$ mouse on a high fat diet, was found in many cells that were positive for amylase (green) (arrowheads in A, B, C) and rarer cells in acini that were either very low or negative for amylase (arrow in B). Hes6 (red anti-lacZ staining) was strongly expressed in islets (Panel D, insulin-blue and amylase-green). Additional analysis using diaminobenzidine staining for Hes6 (brown anti-lacZ staining in D-I) revealed some pancreatic lobules with rare or no extra-islet Hes6$^+$ cells (D), while other lobules contained many such cells (E, F). Duct-associated Hes6$^+$ cells were present (arrow in G), but were much rarer than Hes6$^+$ acinar cells (H, I). Original optical magnification was 120× for A-C, 60× for D-F, and 40× for G-I. A-D are confocal images.

The abnormalities in the Hes6 mutant mouse occur both within and outside of islets. The amylase/insulin double-positive cells and the pancreatic lobule neoformation involves cells outside the islet while the increased cell replication occurs in both compartments. Pancreatic and endocrine regeneration involves precursors expressing Hes6, as shown in FIG. 13. Hes6 expression in stem/progenitor cells serves as a brake on Notch pathway activation, which is required for the high degree of proliferation required for regeneration. In the absence of Hes6, regeneration is triggered by stimuli, e.g., high fat diet, that would not otherwise trigger it at a high level. Because the highly proliferative cells in the new lobules and the increased proliferation in preexisting pancreas appear in the exocrine pancreas as well as the islets, Hes6$^+$ cells should exist outside of the islet. Indeed, there are areas outside of islets that are positive for Hes6 (FIGS. 5e-f, 9). Most of these cells are amylase positive (FIG. 9A-C) but a small subset of duct-associated cells are also Hes6$^+$ (FIG. 9G). The abundance of extra-insular Hes6 positive cells varies strikingly between pancreatic lobules, with some lobules having substantially less than 1% percent extra-islet Hes6+ cells (FIG. 9D) to others with as many as 5% Hes6+ cells (FIG. 9E-F).

Example 8

Hes6 May Play a Role in Maintaining β-Cell Differentiation

Figure 12:
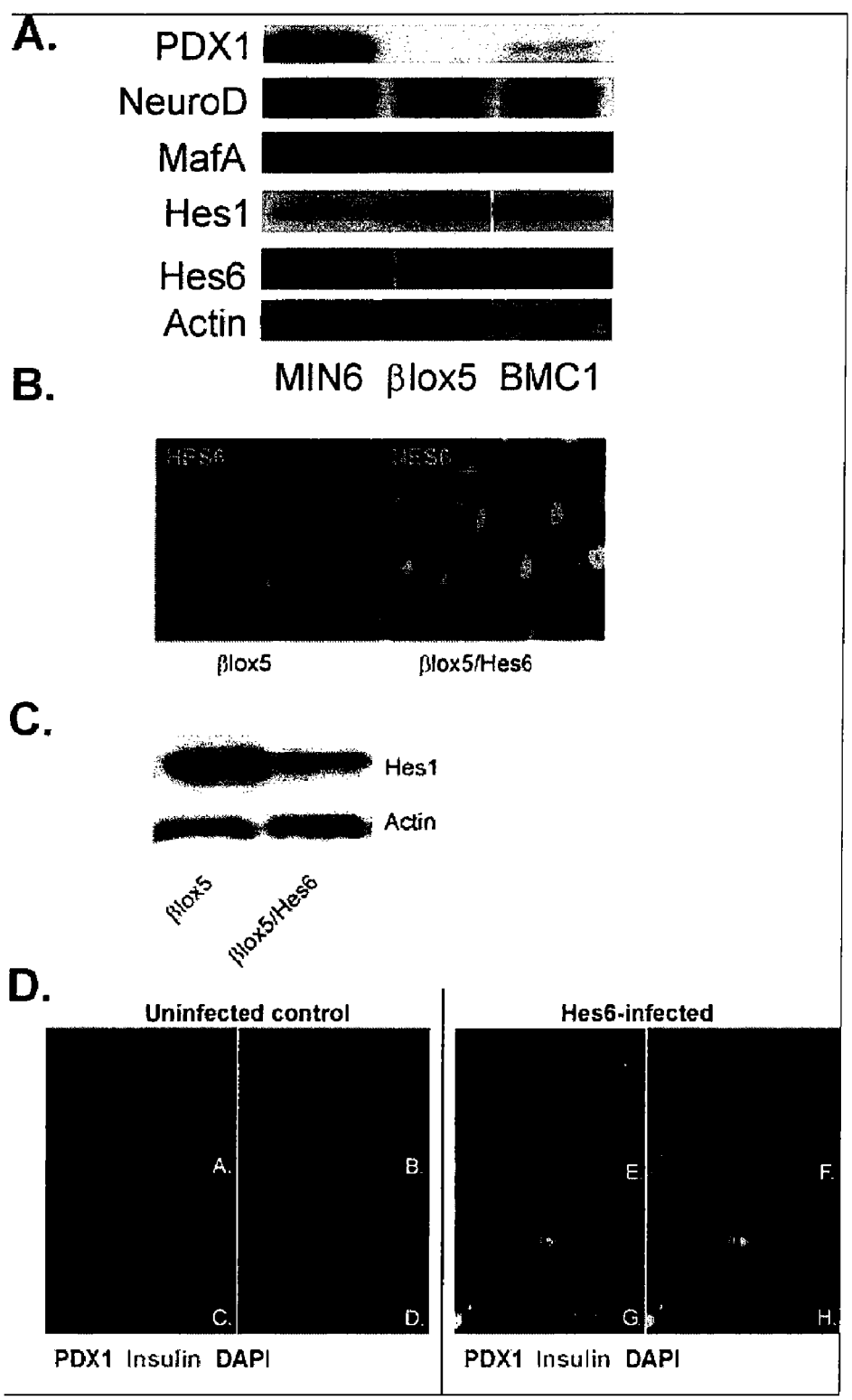
FIG. 12. Hes6 induces insulin expression in a βlox5/MIN6 somatic cell hybrid. A. Western blots were performed on cell extracts from MIN6, βlox5, BMC1 (a MIN6/βlox5 somatic cell hybrid). The blots were probed with polyclonal antibodies to PDX1, NeuroD, MafA, Hes1, Hes6, or β-actin (all recognizing both mouse and human proteins) as a loading control. Hes1 levels were higher and Hes6 levels lower in βlox5 compared with MIN6. Levels in the hybrids reflect the levels in the human cell lines. B. βlox5 was infected with a Hes6 retroviral vector and Hes6 detected by immunostaining. C. Hes6 overexpression resulted in a decrease in Hes1 protein level by Western blot. D. The BMC1 βlox5/MIN6 hybrid was infected with a Hes6 retroviral vector as in C. Control BMC1 cells did not express insulin but Hes6-infected cells did (green staining). This has been repeated in two independent infections and confirmed by RT-PCR. Interestingly, the cells that appear to express insulin are the subpopulation in this hybrid that retain PDX-1 (red staining, all panels). Panels D&H are color combines of red, green and blue channels. Also note that the PDX-1 staining is more intense in the Hes6-infected cells than in controls. Preliminary studies have found that Hes6 induces PDX-1 promoter activity.

When human β-cells were stimulated to enter the cell cycle with hepatocyte growth factor, insulin expression was rapidly shut off (G M Beattie et al., *Diabetes*, 48:1013-9 (1999)). Notch signaling is a strong candidate for playing a role in this process, as it is known to control replication in the developing pancreas (G A Norgaard et al., *Dev Biol*, 264:323-38 (2003); A Hart et al., *Dev Dyn*, 228:185-93 (2003)). Hes1 has been reported to directly inhibit insulin promoter activity (Y Shinozuka et al., *Biochem Biophys Res Commun*, 287:229-35 (2001)). Thus, Hes6, which acts by inhibiting Hes1, can act to promote insulin gene expression. To study the effects of Notch signaling on differentiation, we constructed somatic cell hybrids between the MIN6 mouse insulinoma cell line, which expresses high levels of insulin and low levels of Hes1, and βlox5, a cell line from human β-cells expresses high levels of Hes1 (D Dufayet de la Tour et al., *Mol Endocrinol*, 15:476-483 (2001)) (FIG. 1). The hybrids lost insulin gene expression (not shown), and also exhibited reduced levels of PDX1, NeuroD1, MafA, and Hes6. In contrast, Hes1 was upregulated (FIG. 12A). We were interested to determine whether the changes in Hes1 and Hes6 levels were causal in the dedifferentiation that was observed. To antagonize Hes1 function, βlox5 were infected with a retroviral vector expressing Hes6, resulting in a large increase in Hes6 mRNA and protein (FIG. 12 B) and a decrease in Hes1 protein (FIG. 12C). In the BMC1 somatic cell hybrid between MIN6 and βlox5, which had lost insulin expression, Hes6 was sufficient to induce reversion to an insulin-expressing state (FIG. 12D). This is the first demonstration that Hes6 affects β-cell differentiated function and that Hes6 expression in mature endocrine cells plays a role in maintaining differentiated function while acting as a brake on stimuli that might otherwise activate Notch signaling in those cells. Such an activation could have potentially deleterious effects on endocrine cell function.

Example 9

Ngn3 Directly Activates the Hes6 Promoter

Figure 11:
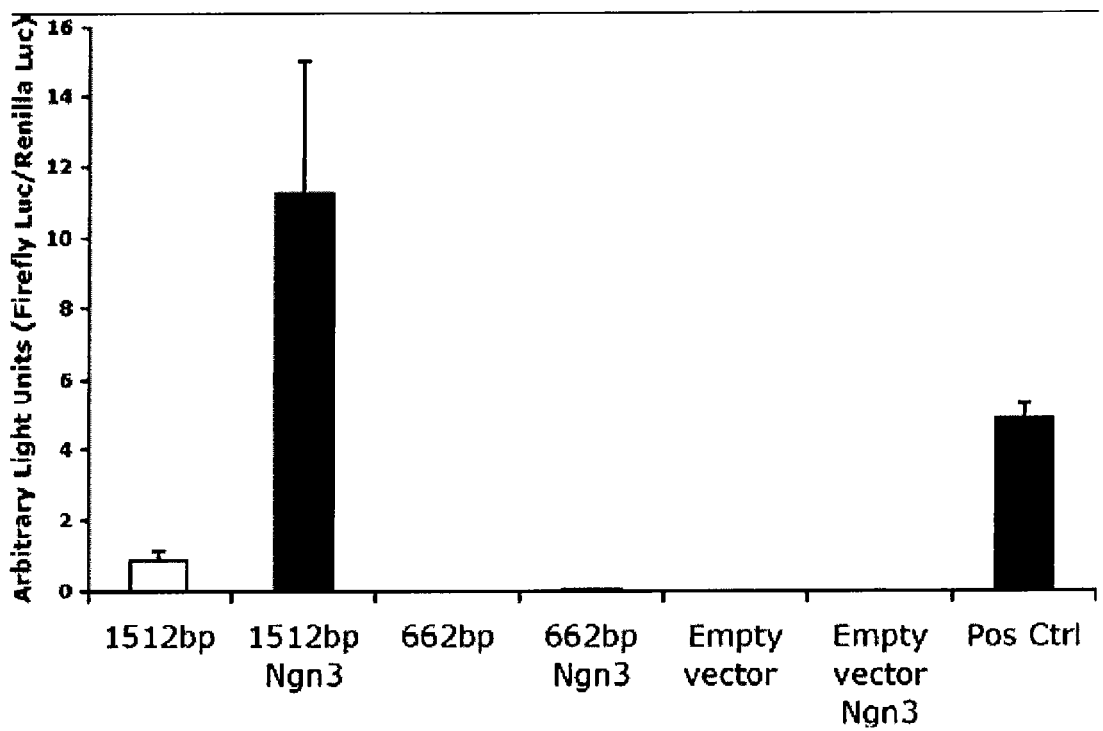
FIG. 11. Ngn3 activates the Hes6 promoter. Two sequences representing 1521 bp and 662 bp of the putative human Hes6 promoter was inserted into pGL3-Basic (Firefly Luciferase reporter vector). HeLa cells were transfected with these constructs with or w/o a CMV-Ngn3 expression vector and a Renilla Luciferase internal control reporter vector. Empty pGL3-Basic and an SV40 promoter/enhancer driving Firefly Luciferase vector (pGL3-Control), were used as negative and positive control, respectively.

A 1512 bp and a 662 bp region upstream of the transcriptional start site of human Hes6 were cloned and inserted into a luciferase reporter vector. These constructs contained most of the human/mouse conserved promoter (FIG. 14). This vector was co-transfected into HeLa cells with a Renilla luciferase control vector and a CMV-Ngn3 expression vector. Ngn3 strongly induced transcription of the 1512 bp Hes6 promoter fragment. However, no induction was observed with the 662 bp fragment, indicating that Ngn3 activates the Hes6 promoter in the region between 662 and 1512 bp upstream of the start-site (FIG. 11). Hes6 is normally not expressed in HeLa cells (not shown). Consequently, these data indicate that Ngn3 is a potent activator of Hes6.

Example 10

Model for Hes6 and Notch-Signaling in Adult Pancreatic Regeneration

Figure 8:
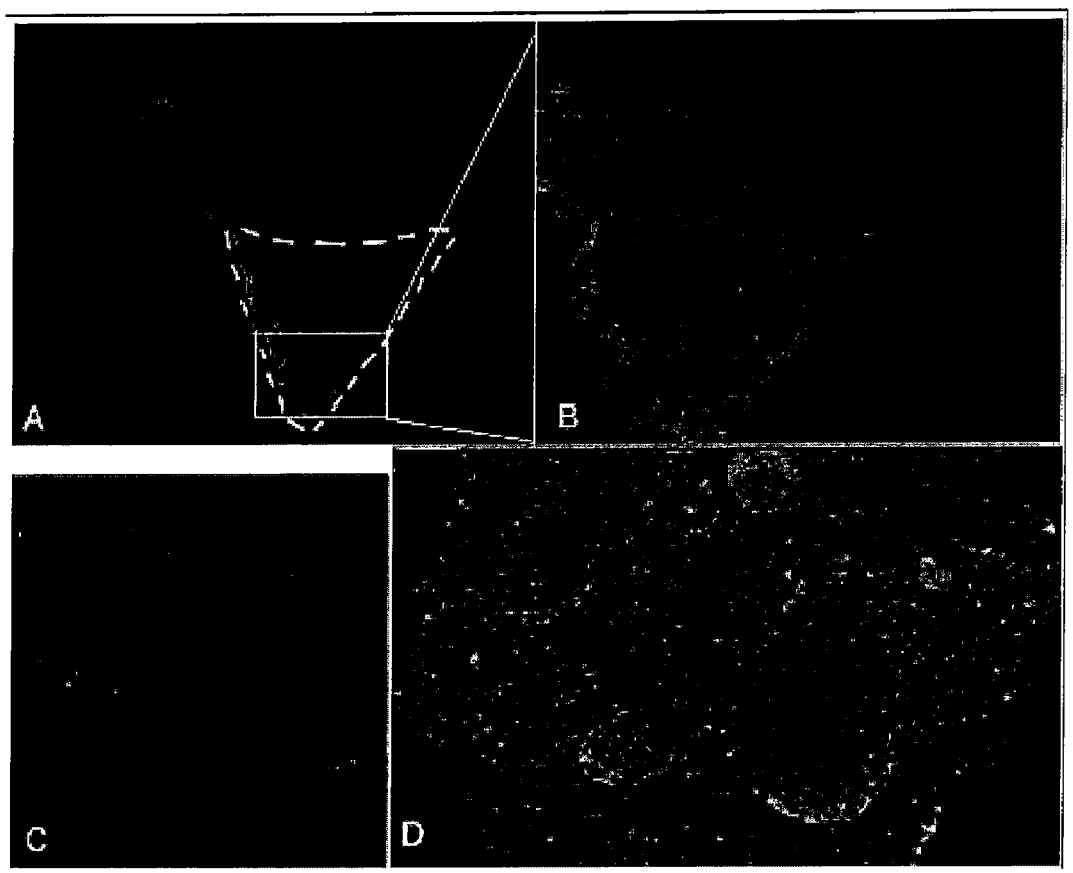
FIG. 8. Neoformation of β-cells in Hes6 mutant pancreata. Hes6 mutant mice where fed a high fat/high calorie diet for 8-10 weeks. The whole pancreas was sectioned and every 100 μm of the pancreata were examined. Normal mice showed no pancreatic abnormalities (not shown). However, a large number of exocrine lobules (encircled in a) presented with abnormal morphology (b-c). The yellow square in a is enlarged in b, demonstrating many cells coexpressing insulin (green) and amylase (red) (co-expression, orange; nuclei-blue). These areas were observed in at least half of the Hes6 mutant pancreatic sections analyzed and were morphologically indistinguishable from acinar pancreas. Amylase/insulin cells are shown in c in high magnification (nuclei are black holes) analyzed with confocal microscopy (amylase-red, insulin-green). Moreover, rare potentially new lobules with extensive proliferation were also observed in Hes6 mutants (d) (Ki-67, blue), limited amylase expression (red) and several large normal insulin-positive (green) islets (nuclei-grey). Such new lobules were never seen in wild-type animals.

The data presented here clearly demonstrate that Hes6 plays an important role in multiple aspects of pancreatic regeneration, both endocrine and non-endocrine. The only known function of Hes6 is to act as a negative regulator of Notch signaling. Thus, the Notch-signaling is important in adult pancreatic regeneration. In the pancreas, Hes6 is induced by Ngn3 in stem/progenitor cells within the pancreas (FIG. 13). Those cells are contained within three compartments: β-cells that can regenerate by replication, a subset of acinar cells, and a rarer subset of duct-associated cells (FIGS. 5, 9). These latter two cell types can give rise to the amylase/insulin double-positive cells and the pancreatic neolobules that are observed in the Hes6 homozygous mutant mice on a high fat diet (FIG. 8).

All publications, patents, patent publications, and Genbank Accession Nos. cited in this specification are herein incorporated by reference as if each individual publication or patent application were specifically and individually indicated to be incorporated by reference.

---

What is claimed is:

1. A method for identifying endocrine stem cells, comprising the steps of
   (a) contacting at least one test cell with a detectable agent specific for Hes6;
   (b) detecting the presence of Hes6 (Hairy/Enhancer of Split 6);
   (c) identifying said test cell as an endocrine stem cell if the presence of Hes6 is detected.

2. The method of claim 1, wherein said detectable agent comprises an anti-Hes6 antibody or a nucleic acid complementary to mRNA encoding Hes6.

* * * * *

UNITED STATES PATENT AND TRADEMARK OFFICE
CERTIFICATE OF CORRECTION

PATENT NO. : 7,776,593 B2 Page 1 of 1
APPLICATION NO. : 11/835391
DATED : August 17, 2010
INVENTOR(S) : Levine and Tyrberg It is certified that error appears in the above-identified patent and that said Letters Patent is hereby corrected as shown below:

On the face page:
In the Assignee data (73): please insert a second assignee as follows:
-- Burnham Institute for Medical Research, Orlando, FL (US) --

Signed and Sealed this

Thirtieth Day of November, 2010

David J. Kappos
*Director of the United States Patent and Trademark Office*

SEQUENCE LISTING

```
<160> NUMBER OF SEQ ID NOS: 1

<210> SEQ ID NO 1
<211> LENGTH: 224
<212> TYPE: PRT
<213> ORGANISM: Homo sapiens
<220> FEATURE:
<223> OTHER INFORMATION: basic helix-loop-helix (bHLH) transcription
      factor, transcriptional repressor hairy/enhancer
      of split 6 (Hes6)

<400> SEQUENCE: 1

Met Ala Pro Pro Ala Ala Pro Gly Arg Asp Arg Val Gly Arg Glu Asp
1               5                   10                  15

Glu Asp Gly Trp Glu Thr Arg Gly Asp Arg Lys Ala Arg Lys Pro Leu
            20                  25                  30

Val Glu Lys Lys Arg Arg Ala Arg Ile Asn Glu Ser Leu Gln Glu Leu
        35                  40                  45
```

-continued

```
Arg Leu Leu Leu Ala Gly Ala Glu Val Gln Ala Lys Leu Glu Asn Ala
     50                  55                  60

Glu Val Leu Glu Leu Thr Val Arg Arg Val Gln Gly Val Leu Arg Gly
 65                  70                  75                  80

Arg Ala Arg Glu Arg Glu Gln Leu Gln Ala Glu Ala Ser Glu Arg Phe
                 85                  90                  95

Ala Ala Gly Tyr Ile Gln Cys Met His Glu Val His Thr Phe Val Ser
             100                 105                 110

Thr Cys Gln Ala Ile Asp Ala Thr Val Ala Ala Glu Leu Leu Asn His
         115                 120                 125

Leu Leu Glu Ser Met Pro Leu Arg Glu Gly Ser Ser Phe Gln Asp Leu
     130                 135                 140

Leu Gly Asp Ala Leu Ala Gly Pro Pro Arg Ala Pro Gly Arg Ser Gly
145                 150                 155                 160

Trp Pro Ala Gly Gly Ala Pro Gly Ser Pro Ile Pro Ser Pro Pro Gly
                 165                 170                 175

Pro Gly Asp Asp Leu Cys Ser Asp Leu Glu Glu Ala Pro Glu Ala Glu
             180                 185                 190

Leu Ser Gln Ala Pro Ala Glu Gly Pro Asp Leu Val Arg Ala Ala Leu
         195                 200                 205

Gly Ala Val Thr Thr Ala Gln Ile Ala Arg Ser Val Trp Arg Pro Trp
210                 215                 220
```